(12) United States Patent
Jensen

(10) Patent No.: US 9,764,003 B2
(45) Date of Patent: Sep. 19, 2017

(54) USE OF LONG-ACTING GLP-1 PEPTIDES

(71) Applicant: Novo Nordisk A/S, Bagsvaerd (DK)

(72) Inventor: Christine B. Jensen, Charlottenlund (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 14/409,493

(22) PCT Filed: Jun. 21, 2013

(86) PCT No.: PCT/EP2013/063004
§ 371 (c)(1),
(2) Date: Dec. 19, 2014

(87) PCT Pub. No.: WO2014/005858
PCT Pub. Date: Jan. 9, 2014

(65) Prior Publication Data
US 2015/0190474 A1 Jul. 9, 2015

Related U.S. Application Data

(60) Provisional application No. 61/694,837, filed on Aug. 30, 2012, provisional application No. 61/708,162, filed on Oct. 1, 2012.

(30) Foreign Application Priority Data

Jul. 1, 2012 (EP) ..................... 12174535
Oct. 1, 2012 (EP) ..................... 12186781

(51) Int. Cl.
*A61K 38/26* (2006.01)
*A61P 5/50* (2006.01)
*A61P 3/04* (2006.01)
*A61P 3/10* (2006.01)

(52) U.S. Cl.
CPC ..................... *A61K 38/26* (2013.01)

(58) Field of Classification Search
None
See application file for complete search history.

(56) References Cited

U.S. PATENT DOCUMENTS

| 8,129,343 | B2 | 3/2012 | Lau et al. |
| 8,536,122 | B2 | 9/2013 | Lau et al. |
| 2010/0047762 | A1 | 2/2010 | Button et al. |
| 2010/0292133 | A1 | 11/2010 | Spetzler et al. |
| 2011/0301080 | A1 | 12/2011 | Bush et al. |

FOREIGN PATENT DOCUMENTS

| CN | 102229668 | | 11/2011 | |
| CN | 102229668 | A | 11/2011 | |
| DK | WO 2006097537 | A2 * | 9/2006 | .......... C07K 14/605 |
| RU | 2409349 | C2 | 1/2011 | |
| RU | 2413530 | C2 | 3/2011 | |
| WO | 2010/092163 | A2 | 8/2010 | |
| WO | 2011/080103 | A1 | 7/2011 | |
| WO | 2011138421 | A1 | 11/2011 | |
| WO | 2012/016419 | A1 | 2/2012 | |
| WO | 2012080471 | A1 | 6/2012 | |
| WO | 2012107476 | A1 | 8/2012 | |
| WO | 2012/130136 | A1 | 10/2012 | |
| WO | 2012/136790 | A1 | 10/2012 | |
| WO | 2012177929 | A2 | 12/2012 | |

OTHER PUBLICATIONS

Kim et al., "Effects of once-weekly dosing of a long-acting release formulation of exenatide on glucose control and body weight in subjects with type 2 diabetes," Diabetes Care 30:1487-1493 (2007).*
Bydureon NDA 022200/S-008 package information, pp. 1-179 (Feb. 2014).*
Clinical Trial NCT00696657, entitled "A Randomised Controlled Clinical Trial in Type 2 Diabetes Comparing Semaglutide to Placebo and Liraglutide," pp. 1-5 (Mar. 11, 2015)—accessed Sep. 24, 2015 at URL clinicaltrials.gov/archive/NCT00696657/2011_03_25.*
Lau et al., "Discovery of the once-weekly glucagon-like peptide-1 (GLP-1) analogue semaglutide," J. Med. Chem. 58:7370-7380 (2015).*
Eperzan assessment report, Euro. Med. Agency, pp. 1-124 (2014)—accessed Sep. 24, 2015 at URL: ema.europa.eu/docs/en_GB/document_library/EPAR_-_Public_assessment_report/human/002735/WC500165119.pdf.*
Trulicity assessment report, Euro. Med. Agency, pp. 1-172 (2014)—accessed Sep. 24, 2015 at URL: ema.europa.eu/docs/en_GB/document_library/EPAR_-_Public_assessment_report/human/002825/WC500179473.pdf).*
CDC, "Nathional Health and Nutrition Examination Survey: Healthy weitght, overweight, and obesity among U.S. adults," 03-0260, pp. 1-2 (Jul. 2003) accessed May 10, 2016 at URL cdc.gov/nchs/data/nhanes/databriefs/adultweight.pdf.*
Madsbad S et al. An Overview of once-weekly glucagon-like peptide-1 receptor agonists available efficacy and safety data and perspectives for the future, Diabetes, Obesity and Metabolism Year 2011, vol. 13, No. 5, pp. 394-407.
Buse B. J. et al., Exenatide once weekly versus liraglutide once daily in patients with type 2 diabetes (DURATION-6): a randomised, open-label study, Lancet, 2013, vol. 381, pp. 117-124.
Mizuta et al. "The Role for GLP-1 in Regulation of Body Weight." Progress in Medicine 2008 vol. 28 No. 8 pp. 1909-1912.

* cited by examiner

*Primary Examiner* — Julie Ha
*Assistant Examiner* — Kristina M Hellman
(74) *Attorney, Agent, or Firm* — Leon Y. Lum

(57) ABSTRACT

The invention relates to use of long-acting GLP-1 peptides in certain dosage regimes for the treatment of type 2 diabetes, obesity, etc.

6 Claims, 6 Drawing Sheets

USE OF LONG-ACTING GLP-1 PEPTIDES

CROSS-REFERENCE TO RELATED APPLICATIONS

This application is a 35 U.S.C. §371 National Stage application of International Application PCT/EP2013/063004 (WO 2014/005858), filed Jun. 21, 2013, which claimed priority of European Patent Application 12174535.0, filed Jul. 1, 2012 and European Patent Application 12186781.6, filed Oct. 1, 2012; this application claims priority under 35 U.S.C. §119 of U.S. Provisional Application 61/694,837; filed Aug. 30, 2012 and U.S. Provisional Application 61/708,162; filed Oct. 1, 2012.

The present invention relates to improved uses of GLP-1 peptides in therapy.

SEQUENCE LISTING

The instant application contains a Sequence Listing which has been submitted in ASCII format via EFS-Web and is hereby incorporated by reference in its entirety. Said ASCII copy, created on Jun. 17, 2013, is named 8545US01_SeqList.txt and is 7,639 bytes in size.

SUMMARY

In one embodiment the invention relates to a method for a) reduction of HbA1c; b) prevention or treatment of type 2 diabetes, hyperglycemia, impaired glucose tolerance, or non-insulin dependent diabetes; or c) prevention or treatment of obesity, reducing body weight and/or food intake, or inducing satiety; wherein said method comprises administration of a GLP-1 agonist to a subject in need thereof, wherein said GLP-1 agonist i) has a half-life of at least 72 hours, wherein said half-life optionally is determined by Assay (II); ii) is administered in an amount of at least 0.7 mg per week, such an amount equivalent to at least 0.7 mg semaglutide per week; and iii) is administered once weekly or less often.

In one embodiment the invention relates to a GLP-1 agonist for use in a) the reduction of HbA1c; b) the prevention or treatment of type 2 diabetes, hyperglycemia, impaired glucose tolerance, or non-insulin dependent diabetes; or c) the prevention or treatment of obesity, for reducing body weight and/or food intake, or for inducing satiety; wherein said use comprises administration of said GLP-1 agonist in an amount of at least 0.7 mg per week, such an amount equivalent to at least 0.7 mg semaglutide per week, and wherein said GLP-1 agonist and/or administration optionally is as defined herein.

In one embodiment the invention relates to a composition comprising a GLP-1 agonist for use in a) the reduction of HbA1c; b) the prevention or treatment of type 2 diabetes, hyperglycemia, impaired glucose tolerance, or non-insulin dependent diabetes; or c) the prevention or treatment of obesity, for reducing body weight and/or food intake, or for inducing satiety; wherein said GLP-1 agonist i) has a half-life of at least 72 hours, wherein said half-life optionally is determined by Assay (II); and ii) is administered in an amount of at least 0.7 mg per week, such an amount equivalent to at least 0.7 mg semaglutide per week; and wherein said composition is administered once weekly or less often, and wherein said GLP-1 agonist and/or administration optionally is as defined herein.

Figure 1:
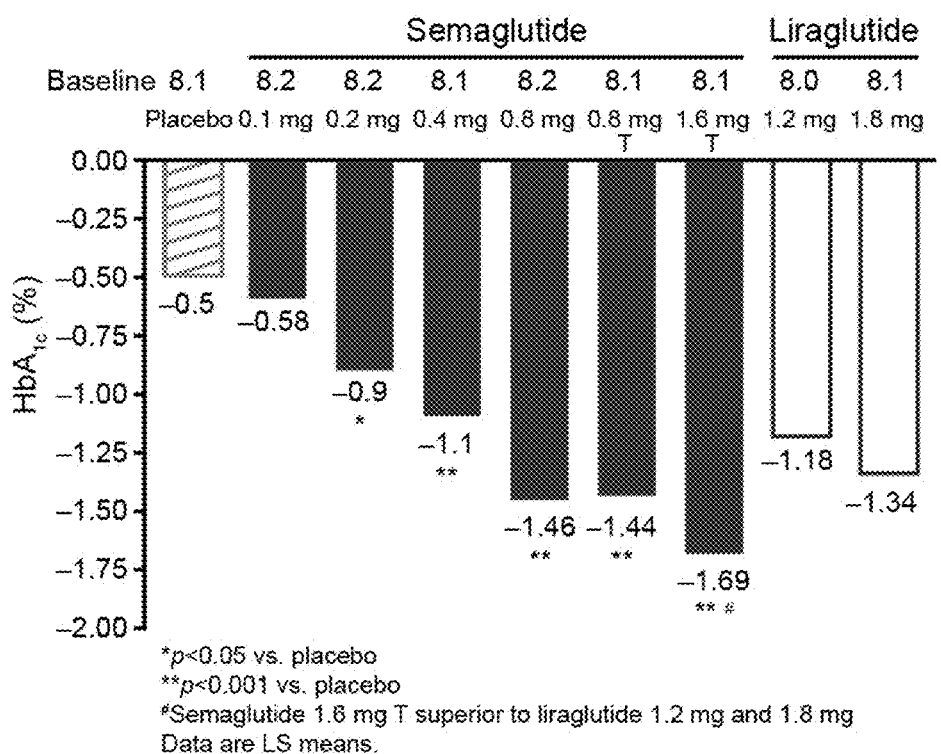
FIG. 1 shows change in HbA1c following subcutaneous administration of placebo, semaglutide, or liraglutide to human subjects. *p<0.05 vs. placebo; **p<0.001 vs. placebo (based on adjusted means). Baseline values are for information only: data are model-adjusted for baseline HbA1c. Data are model-adjusted LS means, FAS LOCF. The estimates are from an ANOVA model with treatment, country and previous treatment as fixed effects and baseline HbA1c as covariate.

SE: Standard error. FAS: Full analysis set. LOCF: Last observation carried forward.

DESCRIPTION

The present invention relates to an improved use of GLP-1 agonists in therapy. In one embodiment the invention relates to certain dosage regimes of GLP-1 agonists which provide improved effect in diseases or conditions, such as prevention and/or treatment of type 2 diabetes and obesity. In one embodiment the methods of the present invention provides surprisingly showed improved reduction of HbA1c and reduction of body weight. In one embodiment the GLP-1 agonist is administered in an amount which provides an improved a) reduction in HbA1c or b) reduction in body weight compared to administration of 1.8 mg liraglutide or less, such as 0.8 mg liraglutide or less, per day.

In one embodiment the invention relates to a method for reduction of HbA1c or for prevention or treatment of type 2 diabetes, hyperglycemia, impaired glucose tolerance, or non-insulin dependent diabetes, said method comprising administration of a GLP-1 agonist to a subject in need thereof in an amount of at least 0.7 mg per week, such an amount equivalent to at least 0.7 mg semaglutide per week. In one embodiment the method is for reduction of HbA1c. In one embodiment the method is for prevention or treatment of type 2 diabetes. In one embodiment the method is for prevention or treatment of hyperglycemia. In one embodiment the method is for prevention or treatment of impaired glucose tolerance. In one embodiment the method is for prevention or treatment of non-insulin dependent diabetes. In one embodiment the method of the invention comprises delaying or preventing diabetic disease progression. In one embodiment a HbA1c level below 7% is achieved. In one embodiment the level of HbA1c is determined according to the method defined by the Diabetes Control and Complications Trial (DCCT). In one embodiment the level of HbA1c is determined according to the method defined by the International Federation of Clinical Chemistry (IFCC).

In one embodiment the invention relates to a method for treating or preventing obesity, for reducing body weight and/or food intake, or for inducing satiety, said method comprising administration of a GLP-1 agonist to a subject in need thereof in an amount of at least 0.7 mg per week, such an amount equivalent to at least 0.7 mg semaglutide per week. In one embodiment the method is for prevention or treatment of obesity. In one embodiment the method is for reducing body weight and/or food intake. In one embodiment the method is for inducing satiety.

In one embodiment the GLP-1 agonist has a half-life of at least 24 hours, such as at least 48 hours, at least 60 hours, or at least 72 hours, or such as at least 84 hours, at least 96 hours, or at least 108 hours, or optionally at least 120 hours, at least 132 hours, or at least 144 hours, wherein said half-life optionally is determined by Assay (II).

In one embodiment the GLP-1 agonist is administered twice weekly or less often, once weekly or less often, or once weekly or less often. In one embodiment the GLP-1 agonist is administered once every secondly week or less often, once every third week or less often, or once a month or less often.

In one embodiment the GLP-1 agonist is administered in an amount per week of at least 0.8 mg, at least 0.9 mg, or at least 1.0 mg. In one embodiment the GLP-1 agonist is administered in an amount per week of at least 1.1 mg, at least 1.2 mg, or at least 1.3 mg. In one embodiment the GLP-1 agonist is administered in an amount per week of at least 1.4 mg, at least 1.5 mg, or at least 1.6 mg.

In one embodiment the GLP-1 agonist is administered in an amount per week equivalent to at least 0.8 mg, at least 0.9 mg, or at least 1.0 mg semaglutide. In one embodiment the GLP-1 agonist is administered in an amount per week equivalent to at least 1.1 mg, at least 1.2 mg, or at least 1.3 mg semaglutide. In one embodiment the GLP-1 agonist is administered in an amount per week equivalent to at least 1.4 mg, at least 1.5 mg, or at least 1.6 mg semaglutide.

In one embodiment the GLP-1 agonist is selected from the group consisting of semaglutide, exenatide, albiglutide, and dulaglutide.

In one embodiment the GLP-1 agonist is administered by parenteral administration, such as subcutaneous injection.

In one embodiment the GLP-1 agonist is a GLP-1 peptide. In one embodiment the GLP-1 peptide comprises no more than 5, such as no more than 4 or no more than 3, amino acid residues which have been substituted, inserted or deleted as compared to GLP-1 (7-37). In one embodiment the GLP-1 peptide comprises no more than 4 amino acid residues which are not encoded by the genetic code.

In one embodiment the GLP-1 peptide is a DPPIV protected GLP-1 peptide. In one embodiment the GLP-1 peptide is DPPIV stabilised.

In one embodiment the GLP-1 agonist has an $EC_{50}$ at or below 3000 pM, such as at or below 500 pM or at or below 100 pM, optionally determined by Assay (I).

In one embodiment the invention relates to a GLP-1 agonist for use in the reduction of HbA1c or for use in the prevention or treatment of type 2 diabetes, hyperglycemia, impaired glucose tolerance, or non-insulin dependent diabetes comprising administering a GLP-1 agonist in an amount of at least 0.7 mg per week, such an amount equivalent to at least 0.7 mg semaglutide per week. In one embodiment the GLP-1 agonist and/or administration is as defined herein.

In one embodiment the invention relates to a GLP-1 agonist for use in the prevention or treatment of obesity, in the reduction of body weight and/or food intake, or in the induction satiety comprising administering a GLP-1 agonist in an amount of at least 0.7 mg per week, such an amount equivalent to at least 0.7 mg semaglutide per week. In one embodiment the GLP-1 agonist and/or administration is as defined herein.

In one embodiment the invention relates to a composition comprising a GLP-1 agonist and one or more pharmaceutically acceptable excipients for use in reduction of HbA1c or for prevention or treatment of type 2 diabetes, hyperglycemia, impaired glucose tolerance, or non-insulin dependent diabetes, wherein said GLP-1 agonist is administered in an amount of at least 0.7 mg per week, such an amount equivalent to at least 0.7 mg semaglutide per week. In one embodiment the GLP-1 agonist and/or administration is as defined herein.

In one embodiment the invention relates to a composition comprising a GLP-1 agonist and one or more pharmaceutically acceptable excipients for use in the prevention or treatment of obesity, in the reduction of body weight and/or food intake, or in the induction satiety, wherein said GLP-1 agonist is administered in an amount of at least 0.7 mg per week, such an amount equivalent to at least 0.7 mg semaglutide per week. In one embodiment the GLP-1 agonist and/or administration is as defined herein.

In one embodiment the GLP-1 agonist is administered with another therapeutic agent. Administration with another therapeutic agent may be carried out as administration of the GLP-1 agonist and the other therapeutic agent within the same therapeutic window (e.g. within a period of two weeks, a period of one week, or in a 96, 72, or 48 hour period, etc.). The treatment with a GLP-1 agonist according to the present invention may be combined with one or more additional therapeutic agents, e.g. selected from antidiabetic agents, anti obesity agents, appetite regulating agents, antihypertensive agents, agents for the treatment and/or prevention of complications resulting from or associated with diabetes and agents for the treatment and/or prevention of complications and disorders resulting from or associated with obesity; examples of these therapeutic agents are: sulphonylureas, thiazolidinediones, biguanides, meglitinides, glucosidase inhibitors, glucagon antagonists, and DPP-IV (dipeptidyl peptidase-IV) inhibitors.

In one embodiment, as used herein, an "amount equivalent to" when used in relation to GLP-1 agonists refers to amounts of a first GLP-1 agonist and a second GLP-1 agonist having GLP-1 receptor potency (i.e. $EC_{50}$) within ±30%, such as within ±20% or within ±10%, of each other optionally determined by Assay (I) described herein and having a half-life within ±30%, such as within ±20% or within ±10%, of each other optionally determined by Assay (II) described herein.

In one embodiment an "effective amount" of a GLP-1 agonist as used herein means an amount sufficient to cure, alleviate, or partially arrest the clinical manifestations of a given disease or state and its complications. An amount adequate to accomplish this is defined as "effective amount". Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician or veterinary.

In one embodiment the term "treatment" or "treating" as used herein means the management and care of a patient for the purpose of combating a condition, such as a disease or a disorder. In one embodiment the term "treatment" or "treating" is intended to include the full spectrum of treatments for a given condition from which the patient is suffering, such as administration of the active compound to alleviate the symptoms or complications; to delay the progression of the disease, disorder, or condition; to alleviate or relieve the symptoms and complications; and/or, to cure or eliminate the disease, disorder, or condition as well as to prevent the condition. In one embodiment prevention is to be understood as the management and care of a patient for the purpose of combating the disease, condition, or disorder and includes the administration of the active compounds to prevent the onset of the symptoms or complications.

In one embodiment the term "hydrophilic spacer" as used herein means a spacer that separates a peptide and an albumin binding residue with a chemical moiety which comprises at least 5 non-hydrogen atoms where 30-50% of these are either N or O.

In one embodiment the term "analogue" as used herein referring to a polypeptide means a modified peptide wherein one or more amino acid residues of the peptide have been substituted by other amino acid residues and/or wherein one or more amino acid residues have been deleted from the peptide and or wherein one or more amino acid residues have been added to the peptide. Such addition or deletion of amino acid residues can take place at the N-terminal of the peptide and/or at the C-terminal of the peptide. A simple system is used to describe analogues: For example Arg$^{34}$GLP-1 (7-37) Lys designates a GLP-1 analogue wherein the naturally occurring lysine at position 34 has been substituted with arginine and a lysine residue has been added to the C-terminal (position 38).

In one embodiment the term "GLP-1 peptide" as used herein means GLP-1 (7-37), a GLP-1 analogue, a GLP-1 derivative or a derivative of a GLP-1 analogue.

In one embodiment the term "exendin-4 peptide" as used herein means exendin-4 (1-39), an exendin-4 analogue, an exendin-4 derivative or a derivative of an exendin-4 analogue.

In one embodiment the term "DPP-IV protected" as used herein referring to a polypeptide means a polypeptide which has been chemically modified in order to render said compound resistant to the plasma peptidase dipeptidyl aminopeptidase-4 (DPP-IV). The DPP-IV enzyme in plasma is known to be involved in the degradation of several peptide hormones, e.g. GLP-1, Exendin-4 etc. Thus a considerable effort is being made to develop GLP-1 agonists less susceptible to DPP-IV mediated hydrolysis in order to reduce the rate of degradation by DPP-IV.

The present invention also relates to a GLP-1 agonist of the invention, for use as a medicament. In particular embodiments, the GLP-1 agonist of the invention may be used for the following medical treatments:

(i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1c;

(ii) delaying or preventing diabetic disease progression, such as progression in type 2 diabetes, delaying the progression of impaired glucose tolerance (IGT) to insulin requiring type 2 diabetes, and/or delaying the progression of non-insulin requiring type 2 diabetes to insulin requiring type 2 diabetes;

(iii) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; and/or delaying gastric emptying.

In another particular embodiment, the indication is (i). In a further particular embodiment the indication is (ii). In a still further particular embodiment the indication is (iii). In one embodiment the indication is type 2 diabetes and/or obesity.

In one embodiment the method comprises prevention, treatment, reduction and/or induction in one or more diseases or conditions defined herein. In one embodiment the indication is (i) and (iii). In one embodiment the indication is (ii) and (iii). In one embodiment the method comprises prevention, treatment, reduction and/or induction in one or more diseases or conditions selected from a) and b), a) and c), b) and c), or a), b) and c) as defined in claim 1.

In one embodiment the invention relates to administration of an effective amount of a GLP-1 agonist.

In one embodiment as used herein, specific values given in relation to numbers or intervals may be understood as the specific value or as about the specific value.

Functional Properties

In a first functional aspect, the GLP-1 agonists of the invention have a good potency. Also, or alternatively, in a second functional aspect, the GLP-1 agonists of the invention have a protracted pharmacokinetic profile. Also, or alternatively, in a third functional aspect, the GLP-1 agonists of the invention are stable against degradation by gastro intestinal enzymes.

Biological Activity (Potency)

According to the first functional aspect, the GLP-1 agonists of the invention are biologically active, or potent. In a particular embodiment, "potency" and/or "activity" refers to in vitro potency, i.e. performance in a functional GLP-1 receptor assay, more in particular to the capability of stimulating cAMP formation in a cell line expressing the cloned human GLP-1 receptor.

The stimulation of the formation of cAMP in a medium containing the human GLP-1 receptor may preferably be determined using a stable transfected cell-line such as BHK467-12A (tk-ts13), and/or using for the determination of cAMP a functional receptor assay, e.g. based on competition between endogenously formed cAMP and exogenously added biotin-labelled cAMP, in which assay cAMP is more preferably captured using a specific antibody, and/or wherein an even more preferred assay is the AlphaScreen cAMP Assay, such as the one described in Assay (I).

In one embodiment the term half maximal effective concentration ($EC_{50}$) generally refers to the concentration which induces a response halfway between the baseline and maximum, by reference to the dose response curve. $EC_{50}$ is used as a measure of the potency of a compound and represents the concentration where 50% of its maximal effect is observed.

The in vitro potency of the GLP-1 agonists of the invention may be determined as described above, and the $EC_{50}$ of the GLP-1 agonist in question determined. The lower the $EC_{50}$, the better the potency.

In a particular embodiment, the medium has the following composition (final in-assay concentrations): 50 mM TRIS-HCl; 5 mM HEPES; 10 mM $MgCl_2$, $6H_2O$; 150 mM NaCl; 0.01% Tween; 0.1% BSA; 0.5 mM IBMX; 1 mM ATP; 1 μM GTP; pH 7.4.

In a further particular embodiment, the GLP-1 agonist of the invention has an in vitro potency corresponding to an $EC_{50}$ at or below 3000 pM, such as below 2000 pM, below 1000 pM, or below 500 pM, or such as below 200 pM or below 100 pM.

In another particular embodiment the GLP-1 agonist of the invention are potent in vivo, which may be determined as is known in the art in any suitable animal model, as well as in clinical trials.

The diabetic db/db mouse is one example of a suitable animal model, and the blood glucose lowering effect may be determined in such mice in vivo, e.g. as described in Assay (III), or as described in Example 43 of WO09/030738.

Also, or alternatively, the effect on food intake in vivo may be determined in pharmacodynamic studies in pigs, e.g. as described in Assay (IV).

Protraction—Half Life In Vivo in Minipigs

According to the second functional aspect, the GLP-1 agonists of the invention are protracted. In a particular embodiment protraction may be determined as half-life ($T_{1/2}$) in vivo in minipigs after i.v. administration. In additional embodiments, the half-life is at least 24 hours, such as at least 48 hours, at least 60 hours, at least 72 hours, or such as at least 84 hours, at least 96 hours, or at least 108 hours.

A suitable assay for determining half-life in vivo in minipigs after i.v. administration is disclosed in Assay (II).

Degradation by Gastro Intestinal Enzymes

According to the third functional aspect, the GLP-1 agonists of the invention are stable, or stabilised, against degradation by one or more gastro intestinal enzymes.

Gastro intestinal enzymes include, without limitation, exo and endo peptidases, such as pepsin, trypsin, chymotrypsin, elastases, and carboxypeptidases. The stability may be tested against these gastro intestinal enzymes in the form of purified enzymes, or in the form of extracts from the gastrointestinal system.

In a particular embodiment, the GLP-1 agonist of the invention has an in vitro half-life ($T_{1/2}$) in an extract of rat small intestines, divided by the corresponding half-life ($T_{1/2}$) of GLP-1 (7-37), of at least 1, such as above 1.0, at least 1.2, at least 2.0, or such as at least 3.0, or at least 4.0. In other words, a ratio (SI) may be defined for each GLP-1 agonist, viz. as the in vitro half-life ($T_{1/2}$) of the GLP-1 agonist in question, in an extract of rat small intestines, divided by the corresponding half-life ($T_{1/2}$) of GLP-1 (7-37).

A suitable assay for determining in vitro half-life in an extract of rat small intestines is disclosed in Assay (V).

GLP-1 Agonists

In one embodiment the GLP-1 peptide comprises an Aib residue in position 8.

In one embodiment the amino acid residue in position 7 of said GLP-1 peptide is selected from the group consisting of D-histidine, desamino-histidine, 2-amino-histidine, β-hydroxy-histidine, homohistidine, $N^α$-acetyl-histidine, α-fluoromethyl-histidine, α-methyl-histidine, 3-pyridylalanine, 2-pyridylalanine and 4-pyridylalanine.

In one embodiment the GLP-1 peptide is attached to a hydrophilic spacer via the amino acid residue in position 23, 26, 34, 36 or 38 relative to the amino acid sequence of GLP-1 (7-37).

In one embodiment the GLP-1 peptide is exendin-4, an exendin-4-analogue, or a derivative of exendin-4.

In one embodiment the GLP-1 agonist peptide comprises the amino acid sequence of the following formula: H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-$NH_2$ (SEQ ID NO: 2).

In one embodiment the GLP-1 agonist comprises an albumin binding residue attached via a hydrophilic spacer to the C-terminal amino acid residue of said GLP-1 peptide.

In one embodiment the GLP-1 agonist comprises a second albumin binding residue is attached to an amino acid residue which is not the C-terminal amino acid residue.

In one embodiment the GLP-1 peptide is selected from the group consisting of semaglutide, albiglutide and dulaglitide.

In one embodiment the GLP-1 peptide has the following structure: His-Aib-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Aib-Arg (SEQ ID NO: 3)

In one embodiment the GLP-1 peptide has the following structure: (His-Gly-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg)2 (SEQ ID NO: 4)—genetically fused to human albumin.

In one embodiment the GLP-1 peptide is dulaglitide.

In one embodiment the GLP-1 agonists of the invention have GLP-1 activity. In one embodiment "a GLP-1 agonist" is understood to refer to any compound, including peptides and non-peptide compounds, which fully or partially activate the human GLP-1 receptor. In one embodiment the "GLP-1 agonist" is any peptide or non-peptide small molecule that binds to a GLP-1 receptor, preferably with an affinity constant ($K_D$) or a potency ($EC_{50}$) of below 1 μM, e. g. below 100 nM as measured by methods known in the art (see e. g., WO 98/08871). In one embodiment methods for identifying GLP-1 agonists are described in WO 93/19175 (Novo Nordisk A/S) and examples of suitable GLP-1 agonists which can be used according to the present invention includes those referred to in WO 2005/027978 (Novo Nordisk A/S), the teachings of which are both incorporated by reference herein. "GLP-1 activity" refers to the ability to bind to the GLP-1 receptor and initiate a signal transduction pathway resulting in insulinotropic action or other physiological effects as is known in the art. For example, the GLP-1 agonists of the invention can be tested for GLP-1 activity using the assay described in Assay (I) herein.

In yet another embodiment the GLP-1 agonist is a stable GLP-1 agonist. As used herein a "stable GLP-1 agonist" means a GLP-1 agonist which exhibits an in vivo plasma elimination half-life of at least 24 hours in man, optionally determined by the method described below. Examples of stable GLP-1 agonists can be found in WO2006/097537.

In one embodiment the method for determination of plasma elimination half-life of a compound in man may be carried out as follows: The compound is dissolved in an isotonic buffer, pH 7.4, PBS or any other suitable buffer. The dose is injected peripherally, preferably in the abdominal or upper thigh. Blood samples for determination of active compound are taken at frequent intervals, and for a sufficient duration to cover the terminal elimination part (e. g., Pre-dose, 1, 2, 3, 4, 5, 6, 7, 8, 10, 12, 24 (day 2), 36 (day 2), 48 (day 3), 60 (day 3), 72 (day 4) and 84 (day 4) hours post dose). Determination of the concentration of active compound is performed as described in Wilken et al., Diabetologia 43 (51), 2000. Derived pharmacokinetic parameters are calculated from the concentration-time data for each individual subject by use of non-compartmental methods, using the commercially available software WinNonlin Version 2.1 (Pharsight, Cary, N.C., USA). The terminal elimination rate constant is estimated by log-linear regression on the terminal log-linear part of the concentration-time curve, and used for calculating the elimination half-life.

In one embodiment the GLP-1 agonist is formulated so as to have a half-life in man of at least 48 hours. This may be obtained by sustained release formulations known in the art.

In one embodiment the GLP-1 agonist is a GLP-1 peptide. In one embodiment the GLP-1 peptide is selected from GLP-1 (7-35), GLP-1 (7-36), GLP-1 (7-36)-amide, GLP-1 (7-37), GLP-1 (7-38), GLP-1 (7-39), GLP-1 (7-40), GLP-1 (7-41) or an analogue or derivative thereof. In one embodiment the GLP-1 peptide comprises no more than 15, such as no more than 10 or no more than 6, amino acid residues which have been substituted, inserted or deleted as compared to GLP-1 (7-37). In one embodiment the GLP-1 peptide comprises no more than 4 amino acid residues which are not encoded by the genetic code. In yet another embodiment, the GLP-1 agonist is exendin-4 or exendin-3, an exendin-4 or exendin-3 analogue, or a derivative of any of these.

In one embodiment the GLP-1 peptide is selected from the group consisting of semaglutide, exenatide, albiglutide, and dulaglitide. In one embodiment the GLP-1 peptide is semaglutide. WO 06/097537 discloses semaglutide (Example 4), a mono-acylated GLP-1 agonist for once weekly administration. In one embodiment the GLP-1 peptide is exenatide. In one embodiment the GLP-1 peptide comprises the amino acid sequence of the formula: H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH$_2$ (SEQ ID NO: 2). Exenatide is a synthetic version of exendin-4, a hormone found in the saliva of the Gila monster. Exenatide displays biological properties similar to GLP-1. In some embodiments the composition is BYDUREON® (a long acting release formula of exenatide in PLGA particles). In one embodiment the "Bydureon® composition" refer to a powder comprising exenatide, poly (D,L-lactide-co-glycolide), and sucrose which immediately prior to injection is reconstituted in a solvent comprising carmellose sodium, sodium chloride, polysorbate 20, monobasic sodium phosphate (e.g. its monohydrate), dibasic sodium phosphate (e.g. its heptahydrate), and water for injections. In one embodiment the GLP-1 peptide has the structure (His-Gly-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg)2 (SEQ ID NO: 4)—genetically fused to human albumin. Albiglutide is a recombinant human serum albumin (HSA)-GLP-1 hybrid protein, likely a GLP-1 dimer fused to HSA. The constituent GLP-1 peptide is analogue, in which Ala at position 8 has been substituted by Glu. In one embodiment the GLP-1 peptide is dulaglitide. Dulaglutide is a GLP-1-Fc construct (GLP-1-linker-Fc from IgG4). In one embodiment the GLP-1 peptide has the structure His-Aib-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Aib-Arg (SEQ ID NO: 3). Liraglutide is a mono-acylated GLP-1 agonist for once daily administration which is marketed as of 2009 by Novo Nordisk A/S, is disclosed in WO 98/08871 Example 37.

In one embodiment the present invention encompasses pharmaceutically acceptable salts of the GLP-1 agonists. Such salts include pharmaceutically acceptable acid addition salts, pharmaceutically acceptable metal salts, ammonium, and alkylated ammonium salts. Also intended as pharmaceutically acceptable acid addition salts are the hydrates which the present GLP-1 agonists are able to form.

In one embodiment the route of administration of GLP-1 agonists may be any route which effectively transports the active compound to the appropriate or desired site of action, such as parenteral. In one embodiment medicaments or pharmaceutical compositions comprising a GLP-1 agonist, such as semaglutide, may be administered parenterally to a patient in need thereof. In one embodiment parenteral administration may be performed by subcutaneous, intramuscular or intravenous injection by means of a syringe, optionally a pen-like syringe.

Alternatively, parenteral administration can be performed by means of an infusion pump. A further option is a composition which may be a powder or a liquid for the administration of a GLP-1 agonist in the form of a nasal or pulmonal spray. As a still further option, the GLP-1 agonist can also be administered transdermally, e.g., from a patch, optionally an iontophoretic patch, or transmucosally, e.g., bucally. The above-mentioned possible ways to administer GLP-1 agonists are not considered as limiting the scope of the invention.

In one embodiment the GLP-1 agonist is co-administered together with a further therapeutically active agent used in the treatments defined herein.

In one embodiment the GLP-1 peptide comprises the amino acid sequence of the formula (I) (SEQ ID NO: 5):

Xaa$_7$-Xaa$_8$-Glu-Gly-Thr-Phe-Thr-Ser-Asp-Xaa$_{16}$-Ser-

Xaa$_{18}$-Xaa$_{19}$Xaa$_{20}$GluXaa$_{22}$-Xaa$_{23}$-Ala-Xaa$_{25}$-Xaa$_{26}$-

Xaa$_{27}$-Phe-Ile-Xaa$_{30}$-Trp-Leu-Xaa$_{33}$-Xaa$_{34}$-Xaa$_{35}$-

Xaa$_{36}$-Xaa$_{37}$-Xaa$_{38}$-Xaa$_{39}$-Xaa$_{40}$-Xaa$_{41}$-Xaa$_{42}$-Xaa$_{43}$-

Xaa$_{44}$-Xaa$_{45}$-Xaa$_{46}$
Formula (I)

wherein
  Xaa$_7$ is L-histidine, D-histidine, desamino-histidine, 2-amino-histidine, β-hydroxy-histidine, homohistidine, N$^\alpha$-acetyl-histidine, α-fluoromethyl-histidine, α-methyl-histidine, 3-pyridylalanine, 2-pyridylalanine or 4-pyridylalanine;
  Xaa$_8$ is Ala, Gly, Val, Leu, Ile, Lys, Aib, (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid, or (1-aminocyclooctyl) carboxylic acid;
  Xaa$_{16}$ is Val or Leu;
  Xaa$_{18}$ is Ser, Lys or Arg;
  Xaa$_{19}$ is Tyr or Gln;
  Xaa$_{20}$ is Leu or Met;
  Xaa$_{22}$ is Gly, Glu or Aib;
  Xaa$_{23}$ is Gln, Glu, Lys or Arg;
  Xaa$_{25}$ is Ala or Val;
  Xaa$_{26}$ is Lys, Glu or Arg;
  Xaa$_{27}$ is Glu or Leu;

Xaa$_{30}$ is Ala, Glu or Arg;
Xaa$_{33}$ is Val or Lys;
Xaa$_{34}$ is Lys, Glu, Asn or Arg;
Xaa$_{35}$ is Gly or Aib;
Xaa$_{36}$ is Arg, Gly or Lys;
Xaa$_{37}$ is Gly, Ala, Glu, Pro, Lys, amide or is absent;
Xaa$_{38}$ is Lys, Ser, amide or is absent;
Xaa$_{39}$ is Ser, Lys, amide or is absent;
Xaa$_{40}$ is Gly, amide or is absent;
Xaa$_{41}$ is Ala, amide or is absent;
Xaa$_{42}$ is Pro, amide or is absent;
Xaa$_{43}$ is Pro, amide or is absent;
Xaa$_{44}$ is Pro, amide or is absent;
Xaa$_{45}$ is Ser, amide or is absent;
Xaa$_{46}$ is amide or is absent;
provided that if Xaa$_{38}$, Xaa$_{39}$, Xaa$_{40}$, Xaa$_{41}$, Xaa$_{42}$, Xaa$_{43}$, Xaa$_{44}$, Xaa$_{45}$ or Xaa$_{46}$ is absent then each amino acid residue downstream is also absent.

In one embodiment the GLP-1 peptide comprises the amino acid sequence of formula (II) (SEQ ID NO: 6):

```
Xaa7-Xaa8-Glu-Gly-Thr-Phe-Thr-Ser-Asp-Val-Ser-
Xaa18-Tyr-Leu-Glu-Xaa22-Xaa23-Ala-Ala-Xaa26-Glu-
Phe-Ile-Xaa30-Trp-Leu-Val-Xaa34-Xaa35-Xaa36-Xaa37Xaa38
Formula (II)
``` wherein
Xaa$_7$ is L-histidine, D-histidine, desamino-histidine, 2-amino-histidine, -hydroxy-histidine, homohistidine, N$^\alpha$-acetyl-histidine, α-fluoromethyl-histidine, α-methyl-histidine, 3-pyridylalanine, 2-pyridylalanine or 4-pyridylalanine;
Xaa$_8$ is Ala, Gly, Val, Leu, Ile, Lys, Aib, (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid, or (1-aminocyclooctyl) carboxylic acid;
Xaa$_{18}$ is Ser, Lys or Arg;
Xaa$_{22}$ is Gly, Glu or Aib;
Xaa$_{23}$ is Gln, Glu, Lys or Arg;
Xaa$_{26}$ is Lys, Glu or Arg; Xaa30 is Ala, Glu or Arg;
Xaa$_{34}$ is Lys, Glu or Arg;
Xaa$_{35}$ is Gly or Aib;
Xaa$_{36}$ is Arg or Lys;
Xaa$_{37}$ is Gly, Ala, Glu or Lys;
Xaa$_{38}$ is Lys, amide or is absent.

In one embodiment the GLP-1 peptide is a DPPIV protected GLP-1 peptide.

In one embodiment the GLP-1 peptide is DPPIV stabilised.

In one embodiment the GLP-1 peptide comprises an Aib residue in position 8.

In one embodiment the amino acid residue in position 7 of said GLP-1 peptide is selected from the group consisting of D-histidine, desamino-histidine, 2-amino-histidine, β-hydroxy-histidine, homohistidine, N$^\alpha$-acetyl-histidine, α-fluoromethyl-histidine, α-methyl-histidine, 3-pyridylalanine, 2-pyridylalanine and 4-pyridylalanine.

In one embodiment the GLP-1 peptide comprises Arg$^{34}$GLP-1 (7-37) or [Aib8,Arg34]GLP-1-(7-37).

In one embodiment the GLP-1 agonist comprises an albumin binding residue which is covalently attached, optionally via a hydrophilic spacer. In one embodiment said albumin binding residue is covalently attached, optionally via a hydrophilic spacer, to the C-terminal amino acid residue of said GLP-1 peptide or an amino acid residue which is not the C-terminal amino acid residue. In one embodiment the GLP-1 peptide is attached to a hydrophilic spacer via the amino acid residue in position 23, 26, 34, 36 or 38 relative to the amino acid sequence of GLP-1 (7-37).

Human Glucagon-Like Peptide-1 is GLP-1 (7-37) and has the sequence HAEGTFTSDVSSYLEGQAAKEFI AWLVKGRG (SEQ ID NO: 1). GLP-1 (7-37) may also be designated "native" GLP-1. In the sequence listing, the first amino acid residue of SEQ ID NO: 1 (histidine) is assigned no. 1. However, in what follows—according to established practice in the art—this histidine residue is referred to as no. 7, and subsequent amino acid residues are numbered accordingly, ending with glycine no. 37. Therefore, generally, any reference herein to an amino acid residue number or a position number of the GLP-1 (7-37) sequence is to the sequence starting with His at position 7 and ending with Gly at position 37. A non-limiting example of a suitable analogue nomenclature is [Aib$^8$,Arg$^{34}$,Lys$^{37}$]GLP-1 (7-37), which designates a GLP-1 (7-37) analogue, in which the alanine at position 8 has been substituted with α-aminoisobutyric acid (Aib), the lysine at position 34 has been substituted with arginine, and the glycine at position 37 has been substituted with lysine.

In one embodiment the GLP-1 agonist exhibits at least 60%, 65%, 70%, 80% or 90% sequence identity to GLP-1 (7-37) over the entire length of GLP-1 (7-37). As an example of a method for determination of sequence identity between two analogues the two peptides [Aib8]GLP-1 (7-37) and GLP-1 (7-37) are aligned. The sequence identity of [Aib8] GLP-1 (7-37) relative to GLP-1 (7-37) is given by the number of aligned identical residues minus the number of different residues divided by the total number of residues in GLP-1 (7-37). Accordingly, in said example the sequence identity is (31-1)/31. In one embodiment non-peptide moieties of the GLP-1 agonist are not included when determining sequence identity.

In one embodiment the GLP-1 agonist is a derivative. In one embodiment the term "derivative" as used herein in the context of a GLP-1 agonist, peptide or analogue means a chemically modified GLP-1 agonist, peptide or analogue, in which one or more substituents have been covalently attached to the agonist, peptide or analogue. The substituent may also be referred to as a side chain. Typical modifications are amides, carbohydrates, alkyl groups, acyl groups, esters and the like. An example of a derivative of GLP-1 (7-37) is N$^{\epsilon26}$-(γ-Glu(N$^\alpha$-hexadecanoyl))-[Arg$^{34}$, Lys$^{25}$]) GLP-1 (7-37).

In a particular embodiment, the side chain is capable of forming non-covalent aggregates with albumin, thereby promoting the circulation of the GLP-1 agonist with the blood stream, and also having the effect of protracting the time of action of the GLP-1 agonist, due to the fact that the aggregate of the GLP-1 agonist and albumin is only slowly disintegrated to release the active pharmaceutical ingredient. Thus, the substituent, or side chain, as a whole may be referred to as an albumin binding moiety.

In particular embodiments, the side chain has at least 10 carbon atoms, or at least 15, 20, 25, 30, 35, or at least 40 carbon atoms. In further particular embodiments, the side chain may further include at least 5 hetero atoms, in particular O and N, for example at least 7, 9, 10, 12, 15, 17, or at least 20 hetero atoms, such as at least 1, 2, or 3 N-atoms, and/or at least 3, 6, 9, 12, or 15 O-atoms.

In another particular embodiment the albumin binding moiety comprises a portion which is particularly relevant for the albumin binding and thereby the protraction, which portion may accordingly be referred to as a protracting moiety. The protracting moiety may be at, or near, the opposite end of the albumin binding moiety, relative to its point of attachment to the peptide.

In a still further particular embodiment the albumin binding moiety comprises a portion inbetween the protracting moiety and the point of attachment to the peptide, which portion may be referred to as a linker, linker moiety, spacer, or the like. The linker may be optional, and hence in that case the albumin binding moiety may be identical to the protracting moiety.

In particular embodiments, the albumin binding moiety and/or the protracting moiety is lipophilic, and/or negatively charged at physiological pH (7.4).

The albumin binding moiety, the protracting moiety, or the linker may be covalently attached to a lysine residue of the GLP-1 peptide by acylation. Additional or alternative conjugation chemistry includes alkylation, ester formation, or amide formation, or coupling to a cysteine residue, such as by maleimide or haloacetamide (such as bromo-/fluoro-/iodo-) coupling.

In one embodiment an active ester of the albumin binding moiety, e.g. comprising a protracting moiety and a linker, is covalently linked to an amino group of a lysine residue, e.g. the epsilon amino group thereof, under formation of an amide bond (this process being referred to as acylation).

Unless otherwise stated, when reference is made to an acylation of a lysine residue, it is understood to be to the epsilon-amino group thereof.

For the present purposes, the terms "albumin binding moiety", "protracting moiety", and "linker" may include the unreacted as well as the reacted forms of these molecules. Whether or not one or the other form is meant is clear from the context in which the term is used.

For the attachment to the GLP-1 agonist, the acid group of the fatty acid, or one of the acid groups of the fatty diacid, forms an amide bond with the epsilon amino group of a lysine residue in the GLP-1 peptide, e.g. via a linker.

In one embodiment the term "fatty acid" refers to aliphatic monocarboxylic acids having from 4 to 28 carbon atoms, it is optionally unbranched, and/or even numbered, and it may be saturated or unsaturated.

In one embodiment the term "fatty diacid" refers to fatty acids as defined above but with an additional carboxylic acid group in the omega position. Thus, fatty diacids are dicarboxylic acids.

Each of the two linkers of the GLP-1 agonist of the invention may comprise the following first linker element:

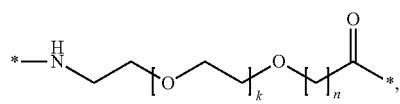

Chem. 5 wherein k is an integer in the range of 1-5, and n is an integer in the range of 1-5.

In a particular embodiment, when k=1 and n=1, this linker element may be designated OEG, or a di-radical of 8-amino-3,6-dioxaoctanic acid, and/or it may be represented by the following formula:

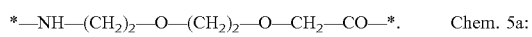

*—NH—(CH$_2$)$_2$—O—(CH$_2$)$_2$—O—CH$_2$—CO—*.   Chem. 5a:

In another particular embodiment, each linker of the GLP-1 agonist of the invention may further comprise, independently, a second linker element, e.g. a Glu di-radical, such as Chem. 6 and/or Chem. 7:

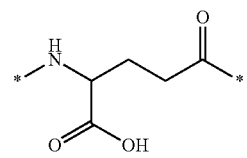

Chem. 6

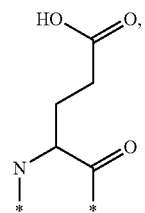

Chem. 7 wherein the Glu di-radical may be included p times, where p is an integer in the range of 1-3.

Chem. 6 may also be referred to as gamma-Glu, or briefly gGlu, due to the fact that it is the gamma carboxy group of the amino acid glutamic acid which is here used for connection to another linker element, or to the epsilon-amino group of lysine. As explained above, the other linker element may, for example, be another Glu residue, or an OEG molecule. The amino group of Glu in turn forms an amide bond with the carboxy group of the protracting moiety, or with the carboxy group of, e.g., an OEG molecule, if present, or with the gamma-carboxy group of, e.g., another Glu, if present.

Chem. 7 may also be referred to as alpha-Glu, or briefly aGlu, or simply Glu, due to the fact that it is the alpha carboxy group of the amino acid glutamic acid which is here used for connection to another linker element, or to the epsilon-amino group of lysine.

The above structures of Chem. 6 and Chem. 7 cover the L-form, as well as the D-form of Glu. In particular embodiments, Chem. 6 and/or Chem. 7 is/are, independently, a) in the L-form, or b) in the D-form.

In still further particular embodiments the linker has a) from 5 to 41 C-atoms; and/or b) from 4 to 28 hetero atoms.

The concentration in plasma of the GLP-1 agonists of the invention may be determined using any suitable method. For example, LC-MS (Liquid Chromatography Mass Spectroscopy) may be used, or immunoassays such as RIA (Radio Immuno Assay), ELISA (Enzyme-Linked Immuno Sorbent Assay), and LOCI (Luminescence Oxygen Channeling Immunoassay). General protocols for suitable RIA and ELISA assays are found in, e.g., WO09/030738 on p. 116-118. A preferred assay is the LOCI (Luminescent Oxygen Channeling Immunoassay), generally as described for the determination of insulin by Poulsen and Jensen in Journal of Biomolecular Screening 2007, vol. 12, p. 240-247—briefly blood samples may be collected at desired intervals, plasma separated, immediately frozen, and kept at −20° C. until analyzed for plasma concentration of the respective GLP-1 agonist; the donor beads are coated with streptavidin, while acceptor beads are conjugated with a monoclonal antibody recognising a mid-/C-terminal epitope of the peptide; another monoclonal antibody, specific for the N-terminus, is biotinylated; the three reactants are combined with the analyte and formed a two-sited immuno-complex; illumination of the complex releases singlet oxygen atoms from the donor beads, which are channeled into the acceptor beads and triggered chemiluminescence which may be measured in an Envision plate reader; the amount of light is proportional to the concentration of the compound.

In one embodiment the term "Aib" as used herein refers to α-aminoisobutyric acid.

Pharmaceutical Compositions

An administered dose may contain from 5 mg-100 mg of the GLP-1 agonist, or from 5-50 mg, or from 5-20 mg, or from 5-10 mg of the GLP-1 agonist.

In one embodiment the composition is BYDUREON® (a long acting release formula of exenatide in PLGA particles).

Pharmaceutical compositions comprising a GLP-1 agonist of the invention or a pharmaceutically acceptable salt, amide, or ester thereof, and a pharmaceutically acceptable excipient may be prepared as is known in the art.

In one embodiment the term "excipient" broadly refers to any component other than the active therapeutic ingredient(s). The excipient may be an inert substance, an inactive substance, and/or a not medicinally active substance. The formulation of pharmaceutically active ingredients with various excipients is known in the art, see e.g. Remington: The Science and Practice of Pharmacy (e.g. 19$^{th}$ edition (1995), and any later editions). Non-limiting examples of excipients are: solvents, diluents, buffers, preservatives, tonicity regulating agents (e.g isotonic agents), chelating agents, stabilisers (e.g. oxidation inhibitors, aggregation inhibitors, surfactants, and/or protease inhibitors).

Examples of formulations include liquid formulations, i.e. aqueous formulations comprising water. A liquid formulation may be a solution, or a suspension. An aqueous formulation typically comprises at least 50% w/w water, or at least 60%, 70%, 80%, or even at least 90% w/w of water.

Alternatively, a pharmaceutical composition may be a solid formulation, e.g. a freeze-dried or spray-dried composition, which may be used as is, or whereto the physician or the patient adds solvents, and/or diluents prior to use.

The pH in an aqueous formulation may be anything between pH 3 and pH 10, for example from about 7.0 to about 9.5; or from about 3.0 to about 7.0.

Still further, a pharmaceutical composition may be formulated as is known in the art of oral formulations of insulinotropic compounds, e.g. using any one or more of the formulations described in WO 2008/145728.

A composition may be administered in several dosage forms, for example as a solution; a suspension; an emulsion; a microemulsion; multiple emulsions; a foam; a salve; a paste; a plaster; an ointment; a tablet; a coated tablet; a chewing gum; a rinse; a capsule such as hard or soft gelatine capsules; a suppositorium; a rectal capsule; drops; a gel; a spray; a powder; an aerosol; an inhalant; eye drops; an ophthalmic ointment; an ophthalmic rinse; a vaginal pessary; a vaginal ring; a vaginal ointment; an injection solution; an in situ transforming solution such as in situ gelling, setting, precipitating, and in situ crystallisation; an infusion solution; or as an implant.

A composition may further be compounded in a drug carrier or drug delivery system, e.g. in order to improve stability, bioavailability, and/or solubility. In a particular embodiment a composition may be attached to such system through covalent, hydrophobic, and/or electrostatic interactions. The purpose of such compounding may be, e.g., to decrease adverse effects, achieve chronotherapy, and/or increase patient compliance.

A composition may also be used in the formulation of controlled, sustained, protracting, retarded, and/or slow release drug delivery systems.

The composition may be administered by parenteral administration. Parenteral administration may be performed by subcutaneous, intramuscular, intraperitoneal, or intravenous injection by means of a syringe, optionally a pen-like syringe, or by means of an infusion pump.

Production Processes

In one embodiment GLP-1 peptides can be produced by appropriate derivatisation of an appropriate peptide backbone which has been produced by recombinant DNA technology or by peptide synthesis (e.g., Merrifield-type solid phase synthesis) as known in the art of peptide synthesis and peptide chemistry.

In one embodiment the production of peptides like GLP-1 (7-37) and GLP-1 analogues is well known in the art. The GLP-1 moiety of the GLP-1 peptide of the invention (or fragments thereof) may for instance be produced by classical peptide synthesis, e.g., solid phase peptide synthesis using t-Boc or Fmoc chemistry or other well established techniques, see, e.g., Greene and Wuts, "Protective Groups in Organic Synthesis", John Wiley & Sons, 1999, Florencio Zaragoza Dörwald, "Organic Synthesis on solid Phase", Wiley-VCH Verlag GmbH, 2000, and "Fmoc Solid Phase Peptide Synthesis", Edited by W. C. Chan and P. D. White, Oxford University Press, 2000.

In one embodiment GLP-1 agonists may be produced by recombinant methods, viz. by culturing a host cell containing a DNA sequence encoding the GLP-1 agonist and capable of expressing the peptide in a suitable nutrient medium under conditions permitting the expression of the peptide. Non-limiting examples of host cells suitable for expression of these peptides are: *Escherichia coli, Saccharomyces cerevisiae*, as well as mammalian BHK or CHO cell lines.

In one embodiment GLP-1 agonists of the invention which include non-natural amino acids and/or a covalently attached N-terminal mono- or dipeptide mimetic may e.g. be produced as described in the experimental part. Or see e.g., Hodgson et al: "The synthesis of peptides and proteins containing non-natural amino acids", Chemical Society Reviews, vol. 33, no. 7 (2004), p. 422-430; and WO 2009/083549 A1 entitled "Semi-recombinant preparation of GLP-1 analogues".

Embodiments

The following are non-limiting embodiments of the invention:

1. A method for reduction of HbA1c or for prevention or treatment of type 2 diabetes, hyperglycemia, impaired glucose tolerance, or non-insulin dependent diabetes, said method comprising administration of a GLP-1 agonist to a subject in need thereof in an amount of at least 0.7 mg per week, such an amount equivalent to at least 0.7 mg semaglutide per week.

2. A method for treating or preventing obesity, for reducing body weight and/or food intake, or for inducing satiety, said method comprising administration of a GLP-1 agonist to a subject in need thereof in an amount of at least 0.7 mg per week, such an amount equivalent to at least 0.7 mg semaglutide per week.

3. The method according to any one of the preceding embodiments, wherein said method comprises delaying or preventing diabetic disease progression.

4. The method according to any one of the preceding embodiments, wherein said GLP-1 agonist has a half-life of at least 24 hours, such as at least 48 hours, at least 60 hours, or at least 72 hours, or such as at least 84 hours, at least 96 hours, or at least 108 hours, or optionally at least 120 hours, at least 132 hours, or at least 144 hours, wherein said half-life optionally is determined by Assay (II).

5. The method according to any one of the preceding embodiments, wherein said GLP-1 agonist is administered twice weekly or less often, once weekly or less often, such as less often than once weekly or once every secondly week or less often, or such as once every third week or less often or once a month or less often.

6. The method according to any one of the preceding embodiments, wherein said GLP-1 agonist is administered in an amount of at least 0.8 mg, at least 1.0 mg, or at least 1.2 mg, such as at least 1.4 mg or at least 1.6 mg, per week.

7. The method according to any one of the preceding embodiments, wherein said GLP-1 agonist is administered in an amount equivalent to at least 0.8 mg, at least 1.0 mg, or at least 1.2 mg, such as at least 1.4 mg or at least 1.6 mg, semaglutide per week. 8. The method according to any one of the preceding embodiments, wherein said GLP-1 agonist is administered in an amount which provides an improved a) reduction in HbA1c or b) reduction in body weight compared to administration of 1.8 mg liraglutide or less, such as 0.8 mg liraglutide or less, per day. 9. The method according to any one of the preceding embodiments, wherein said GLP-1 agonist is selected from the group consisting of semaglutide, exenatide, albiglutide, and dulaglutide.

10. The method according to any one of the preceding embodiments, wherein said GLP-1 agonist is administered by parenteral administration, such as subcutaneous injection.

11. The method according to any one of the preceding embodiments, wherein said GLP-1 agonist is administered simultaneously or sequentially with another therapeutic agent.

12. The method according to any one of any one of the preceding embodiments, wherein the GLP-1 agonist is a GLP-1 peptide.

13. The method according to any one of the preceding embodiments, wherein the GLP-1 peptide comprises the amino acid sequence of the formula (I) (SEQ ID NO: 5):

Xaa$_7$-Xaa$_8$-Glu-Gly-Thr-Phe-Thr-Ser-Asp-Xaa$_{16}$-Ser-

Xaa$_{18}$-Xaa$_{19}$Xaa$_{20}$GluXaa$_{22}$-Xaa$_{23}$-Ala-Xaa$_{25}$-Xaa$_{26}$-

Xaa$_{27}$-Phe-Ile-Xaa$_{30}$-Trp-Leu-Xaa$_{33}$-Xaa$_{34}$-Xaa$_{35}$-

Xaa$_{36}$-Xaa$_{37}$-Xaa$_{38}$-Xaa$_{39}$-Xaa$_{40}$-Xaa$_{41}$-Xaa$_{42}$-Xaa$_{43}$-

Xaa$_{44}$-Xaa$_{45}$-Xaa$_{46}$
Formula (I)

wherein
Xaa$_7$ is L-histidine, D-histidine, desamino-histidine, 2-amino-histidine, β-hydroxy-histidine, homohistidine, N$^\alpha$-acetyl-histidine, α-fluoromethyl-histidine, α-methyl-histidine, 3-pyridylalanine, 2-pyridylalanine or 4-pyridylalanine;

Xaa$_8$ is Ala, Gly, Val, Leu, Ile, Lys, Aib, (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid, or (1-aminocyclooctyl) carboxylic acid;

Xaa$_{16}$ is Val or Leu;
Xaa$_{18}$ is Ser, Lys or Arg;
Xaa$_{19}$ is Tyr or Gln;
Xaa$_{20}$ is Leu or Met;
Xaa$_{22}$ is Gly, Glu or Aib;
Xaa$_{23}$ is Gln, Glu, Lys or Arg;
Xaa$_{25}$ is Ala or Val;
Xaa$_{26}$ is Lys, Glu or Arg;
Xaa$_{27}$ is Glu or Leu;
Xaa$_{30}$ is Ala, Glu or Arg;
Xaa$_{33}$ is Val or Lys;
Xaa$_{34}$ is Lys, Glu, Asn or Arg;
Xaa$_{35}$ is Gly or Aib;
Xaa$_{36}$ is Arg, Gly or Lys;
Xaa$_{37}$ is Gly, Ala, Glu, Pro, Lys, amide or is absent;
Xaa$_{38}$ is Lys, Ser, amide or is absent;
Xaa$_{39}$ is Ser, Lys, amide or is absent;
Xaa$_{40}$ is Gly, amide or is absent;
Xaa$_{41}$ is Ala, amide or is absent;
Xaa$_{42}$ is Pro, amide or is absent;
Xaa$_{43}$ is Pro, amide or is absent;
Xaa$_{44}$ is Pro, amide or is absent;
Xaa$_{45}$ is Ser, amide or is absent;
Xaa$_{46}$ is amide or is absent;
provided that if Xaa$_{38}$, Xaa$_{39}$, Xaa$_{40}$, Xaa$_{41}$, Xaa$_{42}$, Xaa$_{43}$, Xaa$_{44}$, Xaa$_{45}$ or Xaa$_{46}$ is absent then each amino acid residue downstream is also absent.

14. The method according to any one of the preceding embodiments, wherein said polypeptide is a GLP-1 peptide comprising the amino acid sequence of formula (II) (SEQ ID NO: 6):

Xaa$_7$-Xaa$_8$-Glu-Gly-Thr-Phe-Thr-Ser-Asp-Val-Ser-

Xaa$_{18}$-Tyr-Leu-Glu-Xaa22-Xaa$_{23}$-Ala-Ala-Xaa$_{26}$-Glu-

Phe-Ile-Xaa$_{30}$-Trp-Leu-Val-Xaa$_{34}$-Xaa$_{35}$-Xaa$_{36}$-Xaa$_{37}$

Xaa$_{38}$
Formula (II)

wherein
Xaa$_7$ is L-histidine, D-histidine, desamino-histidine, 2-amino-histidine, -hydroxy-histidine, homohistidine, N$^\alpha$-acetyl-histidine, α-fluoromethyl-histidine, α-methyl-histidine, 3-pyridylalanine, 2-pyridylalanine or 4-pyridylalanine;

Xaa$_8$ is Ala, Gly, Val, Leu, Ile, Lys, Aib, (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid, or (1-aminocyclooctyl) carboxylic acid;

Xaa$_{18}$ is Ser, Lys or Arg;
Xaa$_{22}$ is Gly, Glu or Aib;
Xaa$_{23}$ is Gln, Glu, Lys or Arg;
Xaa$_{26}$ is Lys, Glu or Arg; Xaa30 is Ala, Glu or Arg;
Xaa$_{34}$ is Lys, Glu or Arg;
Xaa$_{35}$ is Gly or Aib;
Xaa$_{36}$ is Arg or Lys;
Xaa$_{37}$ is Gly, Ala, Glu or Lys;
Xaa$_{38}$ is Lys, amide or is absent.

15. The method according to any one of the preceding embodiments, wherein said GLP-1 peptide is selected from GLP-1 (7-35), GLP-1 (7-36), GLP-1 (7-36)-amide, GLP-1 (7-37), GLP-1 (7-38), GLP-1 (7-39), GLP-1 (7-40), GLP-1 (7-41) or an analogue or derivative thereof.

16. The method according to any one of the preceding embodiments, wherein said GLP-1 peptide comprises no more than 15, such as no more than 10 or no more than 6, amino acid residues which have been substituted, inserted or deleted as compared to GLP-1 (7-37).

17. The method according to any one of the preceding embodiments, wherein said GLP-1 peptide comprises no more than 5 amino acid residues which have been substituted, inserted or deleted as compared to GLP-1 (7-37).
18. The method according to any one of the preceding embodiments, wherein said GLP-1 peptide comprises no more than 4 amino acid residues which are not encoded by the genetic code.
19. The method according to any one of the preceding embodiments, wherein said GLP-1 peptide is a DPPIV protected GLP-1 peptide.
20. The method according to any one of the preceding embodiments, wherein GLP-1 peptide is DPPIV stabilised.
21. The method according to any one of the preceding embodiments, wherein said GLP-1 peptide comprises an Aib residue in position 8.
22. The method according to any one of the preceding embodiments, wherein the amino acid residue in position 7 of said GLP-1 peptide is selected from the group consisting of D-histidine, desamino-histidine, 2-amino-histidine, β-hydroxy-histidine, homohistidine, N$^\alpha$-acetyl-histidine, α-fluoromethyl-histidine, α-methyl-histidine, 3-pyridylalanine, 2-pyridylalanine and 4-pyridylalanine.
23. The method according to any one of embodiments 7 to 16, wherein said GLP-1 peptide is attached to said hydrophilic spacer via the amino acid residue in position 23, 26, 34, 36 or 38 relative to the amino acid sequence of GLP-1 (7-37).
24. The method according to any one of the preceding embodiments, wherein the GLP-1 peptide is exendin-4, an exendin-4-analogue, or a derivative of exendin-4.
25. The method according to any one of the preceding embodiments, wherein the GLP-1 peptide comprises the amino acid sequence of the following formula: H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly- Ala-Pro-Pro-Pro-Ser-NH$_2$ (SEQ ID NO: 2).
26. The method according to any one of the preceding embodiments wherein one albumin binding residue via said hydrophilic spacer is attached to the C-terminal amino acid residue of said GLP-1 peptide.
27. The method according to any one of the preceding embodiments, wherein a second albumin binding residue is attached to an amino acid residue which is not the C-terminal amino acid residue.
28. The method according to any one of the preceding embodiments, wherein the GLP-1 peptide is selected from the group consisting of semaglutide, albiglutide and dulaglitide.
29. The method according to any one of the preceding embodiments, wherein the GLP-1 peptide has the following structure: His-Aib-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Aib-Arg (SEQ ID NO: 3).
30. The method according to any one of the preceding embodiments, wherein the GLP-1 peptide has the following structure: (His-Gly-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg)2 (SEQ ID NO: 4)—genetically fused to human albumin.
31. The method according to any one of the preceding embodiments wherein the GLP-1 peptide is dulaglitide.
32. The method according to any one of the preceding embodiments wherein the GLP-1 agonist has an EC$_{50}$ at or below 3000 pM, such as at or below 500 pM or at or below 100 pM, optionally determined by Assay (I).
33. A GLP-1 agonist for use in the reduction of HbA1c or for use in the prevention or treatment of type 2 diabetes, hyperglycemia, impaired glucose tolerance, or non-insulin dependent diabetes comprising administering a GLP-1 agonist in an amount of at least 0.7 mg per week, such an amount equivalent to at least 0.7 mg semaglutide per week.
34. A GLP-1 agonist for use in the prevention or treatment of obesity, in the reduction of body weight and/or food intake, or in the induction satiety comprising administering a GLP-1 agonist in an amount of at least 0.7 mg per week, such an amount equivalent to at least 0.7 mg semaglutide per week.
35. A GLP-1 agonist for use according to embodiment 33 or 34, wherein the GLP-1 agonist and/or administration is as defined in any of embodiments 1-32 or 40.
36. A composition comprising a GLP-1 agonist and one or more pharmaceutically acceptable excipients for use in reduction of HbA1c or for prevention or treatment of type 2 diabetes, hyperglycemia, impaired glucose tolerance, or non-insulin dependent diabetes, wherein said GLP-1 agonist is administered in an amount of at least 0.7 mg per week, such an amount equivalent to at least 0.7 mg semaglutide per week.
37. A composition comprising a GLP-1 agonist and one or more pharmaceutically acceptable excipients for use in the prevention or treatment of obesity, in the reduction of body weight and/or food intake, or in the induction satiety, wherein said GLP-1 agonist is administered in an amount of at least 0.7 mg per week, such an amount equivalent to at least 0.7 mg semaglutide per week.
38. A composition for use according to any one of the preceding embodiments, wherein said GLP-1 agonist and/or administration is as defined in any one of embodiments 1-32 or 40.
39. A composition for use according to any one of the preceding embodiments, wherein said composition comprises the Bydureon® composition.
40. The method according to any one of the preceding claims, wherein the method comprises prevention, treatment, reduction or induction in one or more diseases or conditions defined in any one of the previous embodiments.

EXAMPLES

Abbreviations

The following abbreviations are used in the following, in alphabetical order:
ADA: American Diabetes Association Example 1: The Glp-1 Peptide Semaglutide Provides Reduced HbA1c and Body Weight Semaglutide is a unique acylated GLP-1 peptide with a half-life of 160 hours. The aim was to investigate HbA1c dose-response of once-weekly doses of semaglutide (five dose-levels) in subjects with type 2 diabetes. Safety, tolerability and pharmacodynamics of semaglutide versus placebo and open-label once-daily liraglutide were also investigated.
Materials and Methods
Liraglutide may be prepared as described in Example 37 of WO98/08871. Semaglutide may be prepared as described in Example 4 of WO2006/097537. The composition of the GLP-1 agonists administered may be formulated as isotonic aqueous solutions with a phosphate buffer, such as a sodium dihydrogen phosphate buffer, having a pH in the range 7.0-9.0, such as pH 7.4 or pH8.15, for example further comprising the excipients propylene glycol and phenol. The composition of the GLP-1 agonists administered may be as described in WO2003/002136 or WO2005/049061. The placebo composition may be identical to the composition of the GLP-1 agonists, but not containing a GLP-1 agonist.

In a 12-week, randomised, double-blind, placebo-controlled trial, 411 human subjects (n=43-50 per group) with type 2 diabetes were exposed. Participants (male/female 65/35%; baseline HbA1c (mean±SD) 8.1±0.8%; baseline body weight 87.5±13.8 kg; duration of diabetes 2.6±3.1 years; metformin only/diet and exercise alone 80/20%) received subcutaneous injection of one of five semaglutide doses (0.1-1.6 mg) once weekly, open-label liraglutide (1.2 mg, 1.8 mg) once daily, or placebo once weekly. Two of the semaglutide doses were titrated (T) in weekly increments of 0.4 mg. The primary endpoint was change in HbA1c from baseline. Secondary efficacy endpoints included proportion of subjects reaching ADA HbA1c target (<7%) and change in body weight. Change and percentage to target were analysed by ANOVA and logistic regression, respectively. Comparisons between semaglutide and liraglutide were not corrected for multiplicity. Baseline characteristics of the subjects are shown in Table 1.

Figure 3A:
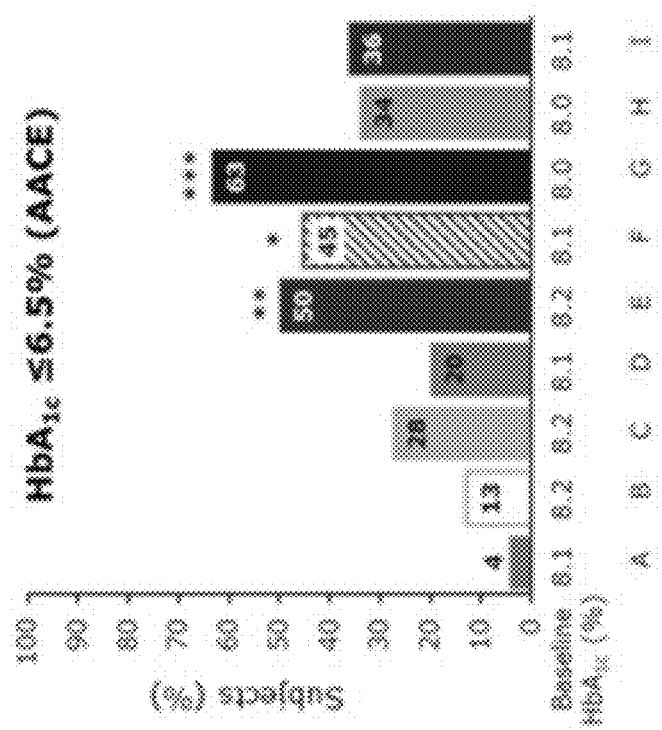
FIG. 3 shows subjects reaching the AACE (FIG. 3A) or ADA (FIG. 3B) criteria for glycaemic control. The number of patients reaching the criteria per treatment is indicated in each bar. The treatments are placebo (A); semaglutide 0.1 mg (B), 0.2 mg (C), 0.4 mg (D), 0.8 mg (E), 0.8 mg T (F), 1.6 mg T (G); liraglutide 1.2 mg (H), 1.8 mg (I). *p<0.05 vs. placebo; p<0.001 vs. placebo; *p<0.0001 vs. placebo (based on adjusted means). Data are FAS LOCF. The estimates are from a logistic regression model treatment, country and previous treatment as fixed effects and baseline HbA1c as covariate. ADA, American Diabetes Association; AACE, American Association of Clinical Endocrinologists.
Figure 3:
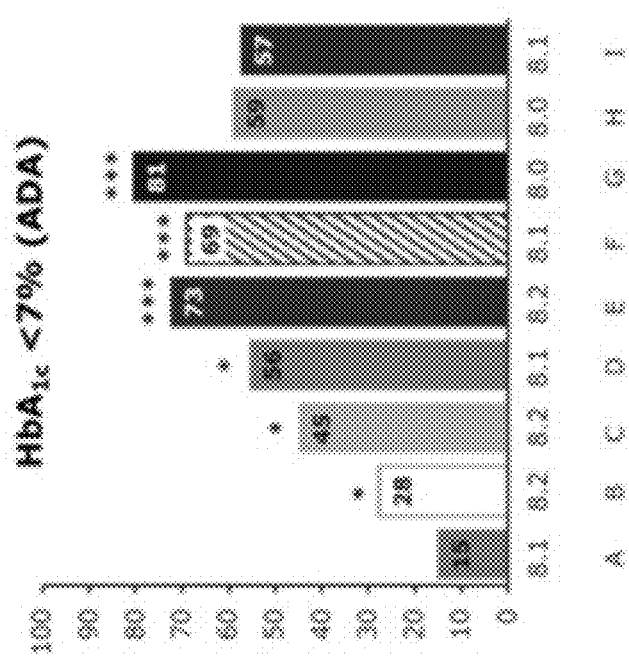

1.2 mg or 1.8 mg; furthermore, treatment with semaglutide 1.6 mg T was statistically superior to treatment with liraglutide 1.2 mg or 1.8 mg with respect to reduction of HbA1c (based on unadjusted means). FIG. 3 shows the percentage and the number of subjects reaching the AACE or ADA criteria for glycaemic control with the different treatments. The results (see FIG. 3) shows that treatment with semaglutide 0.8 mg, 0.8 mg T, or 1.6 mg T improved the percentage and the number of subjects reaching the AACE or ADA criteria for glycaemic control compared to treatment with liraglutide 1.2 mg or 1.8 mg.

Figure 4:
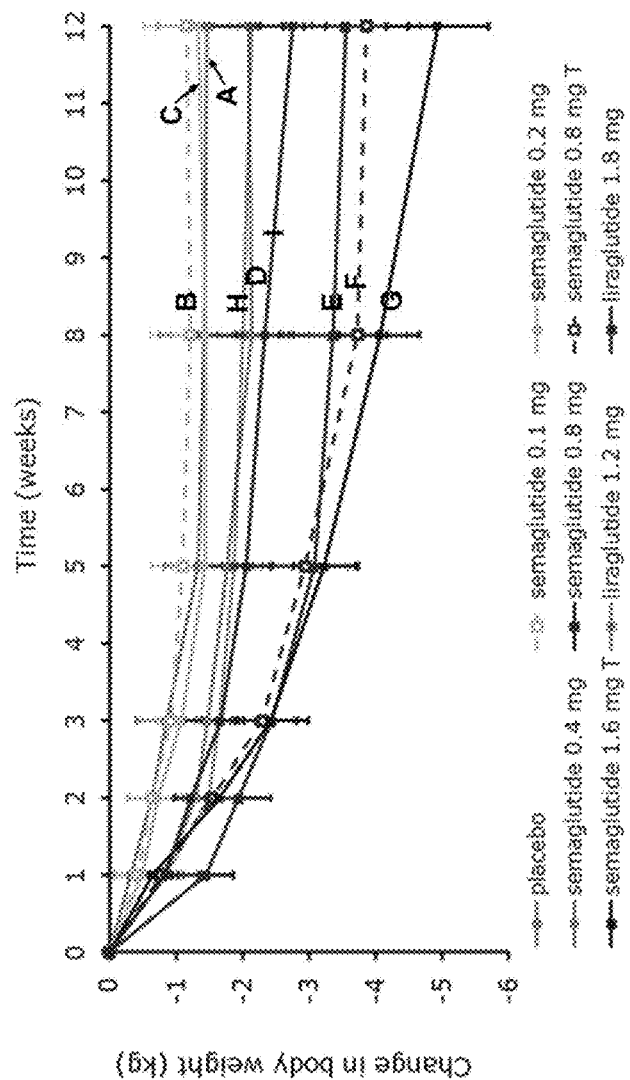
FIG. 4 shows mean body weight change versus time; data are mean (1.96SE), FAS LOCF. The treatments are placebo (A); semaglutide 0.1 mg (B, dashed line), 0.2 mg (C), 0.4 mg (D), 0.8 mg (E), 0.8 mg T (F, dashed line), 1.6 mg T (G); liraglutide 1.2 mg (H), 1.8 mg (I).
Figure 5:
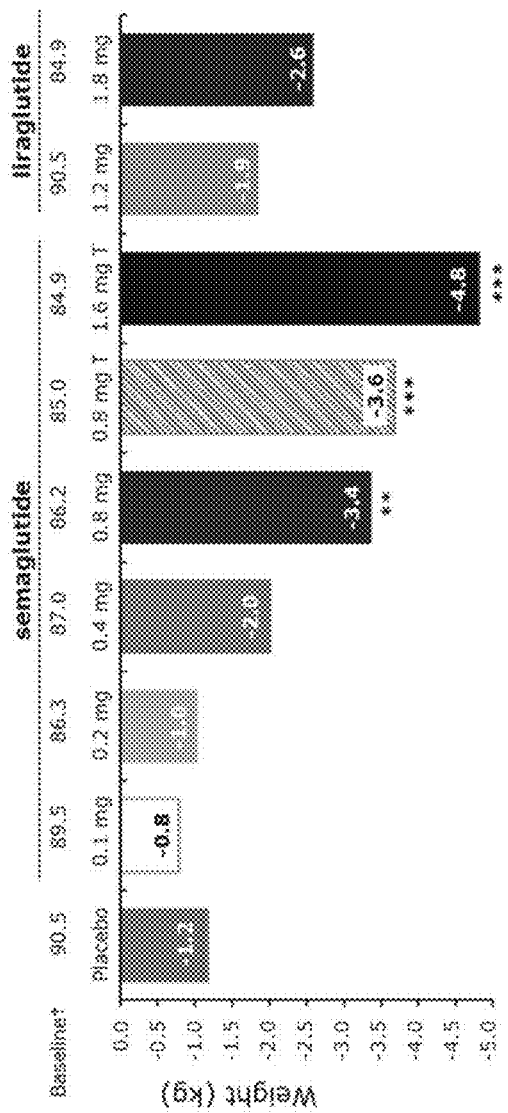
FIG. 5 shows body weight change from baseline at week 12. p<0.001 vs. placebo; *p<0.0001 vs. placebo (based on adjusted means. †: Baseline values for information only: data are model-adjusted for baseline weight. Data are model-adjusted LS means, FAS LOCF. The estimates are from an ANOVA model with treatment, country and previous treatment as fixed effects and baseline weight as covariate.

Body weight was dose-dependently reduced from baseline by up to 4.8 kg vs. placebo 1.2 kg (p<0.01 for doses ≥0.8 mg). FIGS. 4 and 5 shows mean body weight change versus time and body weight change from baseline at week 12, respectively, with the different treatments. The results (see e.g. FIG. 5) shows that treatment with semaglutide 0.8 mg, 0.8 mg T, or 1.6 mg T increased reduction of body weight compared to treatment with liraglutide 1.2 mg or 1.8 mg. Furthermore, the results (see e.g. FIG. 5) shows that treatment with semaglutide 0.8 mg T or 1.6 mg T was statistically superior to treatment with liraglutide 1.8 mg with respect to reduction of body weight; and that treatment with semaglutide 0.8 mg, 0.8 mg T, or 1.6 mg T was statistically

TABLE 1

Baseline characteristics of subjects

| | Placebo | Semaglutide | | | | | | Liraglutide | |
| --- | --- | --- | --- | --- | --- | --- | --- | --- | --- |
| | | 0.1 mg | 0.2 mg | 0.4 mg | 0.8 mg | 0.8 mg T | 1.6 mg T | 1.2 mg | 1.8 mg |
| Exposed* subjects | 46 | 47 | 43 | 48 | 42 | 43 | 47 | 45 | 50 |
| D&E:metformin (%) | 22:78 | 23:77 | 14:86 | 23:77 | 19:81 | 16:84 | 19:81 | 18:82 | 24:76 |
| Female:male (%) | 39:61 | 34:66 | 30:70 | 23:77 | 48:52 | 37:63 | 45:55 | 31:69 | 30:70 |
| Age (years) | 55.3 (10.6) | 55.2 (10.1) | 54.7 (10.0) | 53.8 (10.2) | 55.0 (9.7) | 55.9 (7.9) | 56.4 (10.5) | 54.8 (9.2) | 54.3 (10.1) |
| Duration of diabetes (years) | 2.4 (3.3) | 3.6 (5.0) | 2.3 (2.7) | 2.0 (2.3) | 3.0 (3.0) | 2.6 (2.1) | 1.8 (2.0) | 3.3 (3.4) | 2.5 (2.6) |
| HbA1c (%) | 8.1 (0.8) | 8.2 (0.9) | 8.2 (0.9) | 8.1 (0.9) | 8.2 (0.9) | 8.0 (0.8) | 8.0 (0.7) | 8.0 (0.8) | 8.1 (0.7) |
| FPG (mmol/L) | 8.9 (1.5) | 9.8 (2.7) | 9.5 (2.5) | 9.3 (2.1) | 9.5 (2.4) | 9.6 (2.1) | 9.0 (1.9) | 9.0 (2.3) | 9.3 (2.0) |
| Weight (kg) | 90.5 (13.0) | 89.5 (14.2) | 86.3 (15.1) | 87.0 (14.0) | 85.9 (15.1) | 85.7 (12.6) | 84.5 (14.0) | 90.5 (13.5) | 87.2 (13.1) |
| BMI (kg/m$^2$) | 31.7 (3.8) | 31.5 (4.6) | 30.4 (3.9) | 29.7 (4.5) | 30.7 (4.5) | 31.2 (4.2) | 30.9 (4.7) | 31.0 (4.6) | 30.9 (4.6) |

Data are mean (SD) unless otherwise stated.
*Number of subjects exposed to actual treatment.
D&E: Diet and exercise.
FPG: Fasting plasma glucose.
BMI: Body mass index.

Results

Figure 2:
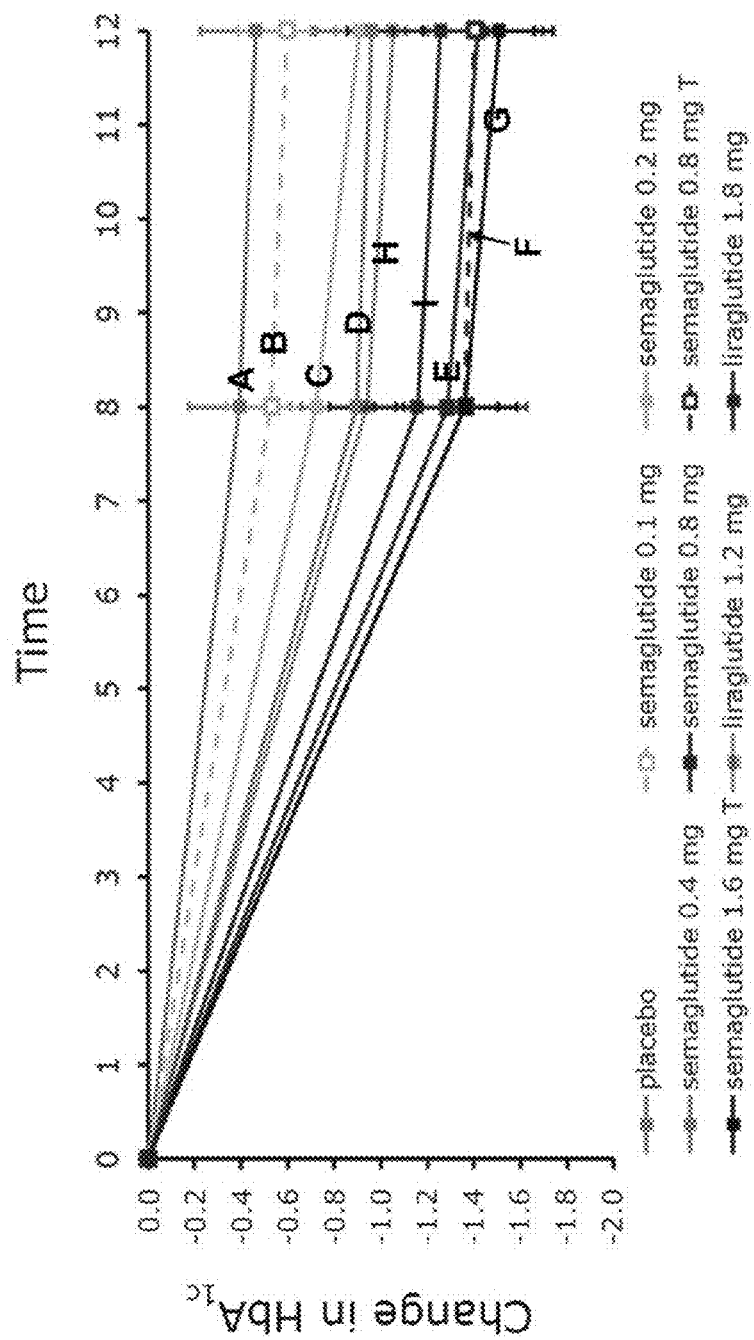
FIG. 2 shows mean change in HbA1c from baseline versus time; data are mean (1.96SE), FAS LOCF. The treatments are placebo (A); semaglutide 0.1 mg (B, dashed line), 0.2 mg (C), 0.4 mg (D), 0.8 mg (E), 0.8 mg T (F, dashed line), 1.6 mg T (G); liraglutide 1.2 mg (H), 1.8 mg (I).

In the full analysis set, semaglutide (≥0.2 mg) dose-dependently reduced HbA1c from baseline (FIG. 1), and increased the likelihood of achieving HbA1c<7% (p<0.05 vs. placebo for doses ≥0.2 mg). The results with respect to change in HbA1c are shown in FIG. 1. The change in HbA1c in FIG. 1 is from baseline at week 12. FIG. 2 shows the change in HbA1c over time with the different treatments. Treatment with semaglutide ≥0.8 mg numerically brought more patients to target than liraglutide 1.8 mg (0.8 mg T 69%, 0.8 mg 73%, 1.6 mg T 81% vs. liraglutide 1.8 mg 57%). The results (see e.g. FIG. 1) shows that treatment with semaglutide 0.8 mg, 0.8 mg T, or 1.6 mg T improved reduction of HbA1c compared to treatment with liraglutide superior to liraglutide 1.2 mg with respect to reduction of body weight (based on unadjusted means).

There were no reports of pancreatitis or treatment-related changes in blood calcitonin. Proportion of subjects with nausea and vomiting increased with dose, but were generally mild or moderate and ameliorated by titration. Withdrawals due to gastrointestinal adverse events were 4.7%-27.7% for semaglutide and 2.2%-10% for liraglutide. Few subjects reported minor hypoglycaemia (semaglutide n=5, liraglutide n=3); no major hypoglycaemia. Injection site reactions were reported by 7 subjects: semaglutide n=2; liraglutide n=5. One subject (semaglutide 1.6 mg T) developed low titre non-neutralising anti-semaglutide antibodies (no cross-reaction to native GLP-1).

Conclusion

Over 12 weeks, semaglutide dose-dependently reduced HbA1c and body weight. The effect of semaglutide 0.4 mg on glycaemic control and body weight was comparable to that of liraglutide 1.2 mg, while semaglutide ≥0.8 mg appeared to bring more subjects to target and provided better weight loss than liraglutide 1.8 mg. No semaglutide safety concerns were identified. Dose escalation was not a major focus of this trial and it will be optimised in future clinical trials.

Pharmacological Methods

Assay (I): In Vitro Potency

The purpose of this example is to test the activity, or potency, of GLP-1 agonists in vitro. The potencies of GLP-1 agonists may be determined as described below, i.e. as the stimulation of the formation of cyclic AMP (cAMP) in a medium containing membranes expressing the human GLP-1 receptor.

Principle

Purified plasma membranes from a stable transfected cell line, BHK467-12A (tk-ts13), expressing the human GLP-1 receptor are stimulated with the GLP-1 agonist in question, and the potency of cAMP production is measured using the AlphaScreen™ cAMP Assay Kit from Perkin Elmer Life Sciences. The basic principle of The AlphaScreen Assay is a competition between endogenous cAMP and exogenously added biotin-cAMP. The capture of cAMP is achieved by using a specific antibody conjugated to acceptor beads.

Cell Culture and Preparation of Membranes

A stable transfected cell line and a high expressing clone are selected for screening. The cells are grown at 5% $CO_2$ in DMEM, 5% FCS, 1% Pen/Strep (Penicillin/Streptomycin) and 0.5 mg/ml of the selection marker G418. Cells at approximate 80% confluence are washed 2× with PBS and harvested with Versene (aqueous solution of the tetrasodium salt of ethylenediaminetetraacetic acid), centrifuged 5 min at 1000 rpm and the supernatant removed. The additional steps are all made on ice. The cell pellet is homogenised by the Ultrathurax for 20-30 sec. in 10 ml of Buffer 1 (20 mM Na-HEPES, 10 mM EDTA, pH=7.4), centrifuged 15 min at 20,000 rpm and the pellet resuspended in 10 ml of Buffer 2 (20 mM Na-HEPES, 0.1 mM EDTA, pH=7.4). The suspension is homogenised for 20-30 sec and centrifuged 15 min at 20,000 rpm. Suspension in Buffer 2, homogenisation and centrifugation is repeated once and the membranes are resuspended in Buffer 2. The protein concentration is determined and the membranes stored at −80° C. until use.

The assay is performed in ½-area 96-well plates, flat bottom (e.g. Costar cat. no: 3693). The final volume per well is 50 µl.

Solutions and Reagents

Exemplary solutions and reagents are given below.

AlphaScreen cAMP Assay Kit from Perkin Elmer Life Sciences (cat. No: 6760625M); containing Anti-cAMP Acceptor beads (10 U/µl), Streptavidin Donor beads (10 U/µl) and Biotinylated-cAMP (133 U/µl).

AlphaScreen Buffer, pH=7.4: 50 mM TRIS-HCl (Sigma, cat. no: T3253); 5 mM HEPES (Sigma, cat. no: H3375); 10 mM $MgCl_2$, $6H_2O$ (Merck, cat. no: 5833); 150 mM NaCl (Sigma, cat. no: S9625); 0.01% Tween (Merck, cat. no: 822184). The following was added to the AlphaScreen Buffer prior to use (final concentrations indicated): BSA (Sigma, cat. no. A7906): 0.1%; IBMX (Sigma, cat. no. 15879): 0.5 mM; ATP (Sigma, cat. no. A7699): 1 mM; GTP (Sigma, cat. no. G8877): 1 µM.

cAMP standard (dilution factor in assay=5): cAMP Solution: 5 µL of a 5 mM cAMP-stock+495 µL AlphaScreen Buffer.

Suitable dilution series in AlphaScreen Buffer are prepared of the cAMP standard as well as the GLP-1 agonist to be tested, e.g. the following eight concentrations of the GLP-1 agonist: $10^{-7}$, $10^{-8}$, $10^{-9}$, $10^{-10}$, $10^{-11}$, $10^{-12}$, $10^{-13}$ and $10^{-14}$ M, and a series from, e.g., $10^{-6}$ to $3 \times 10^{-11}$ of cAMP.

Membrane/Acceptor Beads

Use hGLP-1/BHK 467-12A membranes; 6 µg/well corresponding to 0.6 mg/ml (the amount of membranes used pr. well may vary)

"No membranes": Acceptor Beads (15 µg/ml final) in AlphaScreen buffer

"6 µg/well membranes": membranes+Acceptor Beads (15 µg/ml final) in AlphaScreen buffer Add 10 µl "No membranes" to the cAMP standard (per well in duplicates) and the positive and negative controls Add 10 µl "6 µg/well membranes" to GLP-1 and GLP-1 agonists (per well in duplicates/triplicates)

Pos. Control: 10 µl "no membranes"+10 µl AlphaScreen Buffer

Neg. Control: 10 µl "no membranes"+10 µl cAMP Stock Solution (50 µM)

As the beads are sensitive to direct light, any handling is in the dark (as dark as possible), or in green light. All dilutions are made on ice.

Procedure

1. Make the AlphaScreen Buffer.
2. Dissolve and dilute the GLP-1 agonists/cAMP standard in AlphaScreen Buffer.
3. Make the Donor Beads solution and incubate 30 min. at RT.
4. Add the cAMP/GLP-1 agonists to the plate: 10 µl per well.
5. Prepare membrane/Acceptor Beads solution and add this to the plates: 10 µl per well.
6. Add the Donor Beads: 30 µl per well.
7. Wrap the plate in aluminum foil and incubate on the shaker for 3 hours (very slowly) at RT.
8. Count on AlphaScreen—each plate pre incubates in the AlphaScreen for 3 minutes before counting.

The $EC_{50}$ [pM] values may be calculated using the GraphPad Prism software (version 5). If desired, the fold variation in relation to GLP-1 may be calculated as $EC_{50}$ (GLP-1)/ $EC_{50}$ (analogue)−3693.2.

Assay (II): Half-Life in Minipigs

The purpose of this study is to determine the protraction in vivo of GLP-1 agonists after i.v. administration to minipigs, i.e. the prolongation of their time of action. This is done in a pharmacokinetic (PK) study, where the terminal half-life of the GLP-1 agonist in question is determined. By terminal half-life is generally meant the period of time it takes to halve a certain plasma concentration, measured after the initial distribution phase.

Male Göttingen minipigs are obtained from Ellegaard Göttingen Minipigs (Dalmose, Denmark) approximately 7-14 months of age and weighing from approximately 16-35 kg are used in the studies. The minipigs are housed individually and fed restrictedly once or twice daily with SDS minipig diet (Special Diets Services, Essex, UK). After at least 2 weeks of acclimatisation two permanent central venous catheters are implanted in vena cava caudalis or cranialis in each animal. The animals are allowed 1 week recovery after the surgery, and are then used for repeated pharmacokinetic studies with a suitable wash-out period between dosings.

The animals are fasted for approximately 18 h before dosing and for at least 4 h after dosing, but have ad libitum access to water during the whole period.

The GLP-1 agonist is dissolved in 50 mM sodium phosphate, 145 mM sodium chloride, 0.05% tween 80, pH 7.4 to a concentration of usually from 20-60 nmol/ml. Intravenous injections (the volume corresponding to usually 1-2 nmol/kg, for example 0.033 ml/kg) of the compounds are given through one catheter, and blood is sampled at predefined time points for up till 13 days post dosing (preferably through the other catheter). Blood samples (for example 0.8 ml) are collected in EDTA buffer (8 mM) and then centrifuged at 4° C. and 1942 G for 10 minutes. Plasma is pippetted into Micronic tubes on dry ice, and kept at −20° C. until analyzed for plasma concentration of the respective GLP-1 compound using ELISA or a similar antibody based assay or LC-MS. Individual plasma concentration-time profiles are analyzed by a non-compartmental model in WinNonlin v. 5.0 (Pharsight Inc., Mountain View, Calif., USA), and the resulting terminal half-lives (harmonic mean) determined.

Assay (III): Effect on Blood Glucose and Body Weight

The purpose of the study is to verify the effect of GLP-1 agonists on blood glucose (BG) and body weight (BW) in a diabetic setting. GLP-1 agonists may be tested in a dose-response study in an obese, diabetic mouse model (db/db mice) as described in the following.

Fifty db/db mice (Taconic, Denmark), fed from birth with the diet NIH31 (NIH 31M Rodent Diet, commercially available from Taconic Farms, Inc., US, see www.taconic.com), are enrolled for the study at the age of 7-9 weeks The mice are given free access to standard chow (e.g. Altromin 1324, Brogaarden, Gentofte, Denmark) and tap water and kept at 24° C. After 1-2 weeks of acclimatisation, the basal blood glucose is assessed twice on two consecutive days (i.e. at 9 am). The 8 mice with the lowest blood glucose values may be excluded from the experiments. Based on the mean blood glucose values, the remaining 42 mice may be selected for further experimentation and allocated to 7 groups (n=6) with matching blood glucose levels. The mice may be used in experiments with duration of 5 days for up to 4 times. After the last experiment the mice are euthanised.

The seven groups may receive treatment as follows:
1: Vehicle, subcutaneous
2: GLP-1 agonist, 0.3 nmol/kg, subcutaneous
3: GLP-1 agonist, 1.0 nmol/kg, subcutaneous
4: GLP-1 agonist, 3.0 nmol/kg, subcutaneous
5: GLP-1 agonist, 10 nmol/kg, subcutaneous
6: GLP-1 agonist, 30 nmol/kg, subcutaneous
7: GLP-1 agonist, 100 nmol/kg, subcutaneous
Vehicle: 50 mM sodium phosphate, 145 mM sodium chloride, 0.05% tween 80, pH 7.4.

The GLP-1 agonist is dissolved in the vehicle, e.g. to concentrations of 0.05, 0.17, 0.5, 1.7, 5.0 and 17.0 nmol/ml. Animals are dosed subcutaneous with a dose-volume of 6 ml/kg (i.e. 300 µl per 50 g mouse).

On the day of dosing, blood glucose is assessed at time −½ h (8.30 am), where after the mice are weighed. The GLP-1 agonist is dosed at approximately 9 am (time 0). On the day of dosing, blood glucose is assessed e.g. at times 1, 2, 4 and 8 h (10 am, 11 am, 1 pm and 5 pm).

On the following days, the blood glucose is assessed e.g. at time 24, 48, 72, and 96 h after dosing (i.e. at 9 am on day 2, 3, 4, 5). On each day, the mice are weighed following blood glucose sampling.

The mice are weighed individually on a digital weight.

Samples for the measurement of blood glucose are obtained from the tail tip capillary of conscious mice. Blood, 10 µl, is collected into heparinised capillaries and transferred to 500 µl glucose buffer (EKF system solution, Eppendorf, Germany). The glucose concentration is measured using the glucose oxidase method (glucose analyser Biosen 5040, EKF Diagnostic, GmbH, Barleben, Germany). The samples are kept at room temperature for up to 1 h until analysis. If analysis has to be postponed, samples are kept at 4° C. for a maximum of 24 h.

$ED_{50}$ is the dose giving rise to half-maximal effect in nmol/kg. This value is calculated on the basis of the ability of the GLP-1 agonists to lower body weight as well as the ability to lower blood glucose, as explained below.

$ED_{50}$ for body weight is calculated as the dose giving rise to half-maximum effect on delta BW 24 hours following the subcutaneous administration of the GLP-1 agonist. For example, if the maximum decrease in body weight after 24 hours is 4.0 g, then $ED_{50}$ bodyweight would be that dose in nmol/kg which gives rise to a decrease in body weight after 24 hours of 2.0 g. This dose ($ED_{50}$ body weight) may be read from the dose-response curve.

$ED_{50}$ for blood glucose is calculated as the dose giving rise to half-maximum effect on AUC delta BG 8 hours following the subcutaneous administration of the GLP-1 agonist.

The $ED_{50}$ value may only be calculated if a proper sigmoidal dose-response relationship exists with a clear definition of the maximum response. Thus, if this would not be the case the GLP-1 agonist in question is re-tested in a different range of doses until the sigmoidal dose-response relationship is obtained.

Assay (IV): Effect on Food Intake

The purpose of this experiment is to investigate the effect of GLP-1 agonists on food intake in pigs. This is done in a pharmacodynamic (PD) study as described below, in which food intake is measured 1, 2, 3, and 4 days after administration of a single dose of the GLP-1 agonist, as compared to a vehicle-treated control group.

Female Landrace Yorkshire Duroc (LYD) pigs, approximately 3 months of age, weighing approximately 30-35 kg are used (n=3-4 per group). The animals are housed in a group for 1-2 weeks during acclimatisation to the animal facilities. During the experimental period the animals are placed in individual pens from Monday morning to Friday afternoon for measurement of individual food intake. The animals are fed ad libitum with pig fodder (Svinefoder, Antonio) at all times both during the acclimatisation and the experimental period. Food intake is monitored on line by logging the weight of fodder every 15 minutes. The system used is Mpigwin (Ellegaard Systems, Faaborg, Denmark).

The GLP-1 agonists are dissolved in a phosphate buffer (50 mM phosphate, 0.05% tween 80, pH 8) e.g. at concentrations of 12, 40, 120, 400 or 1200 nmol/ml corresponding to doses of 0.3, 1, 3, 10, or 30 nmol/kg. The phosphate buffer served as vehicle. Animals are dosed with a single subcutaneous dose of the GLP-1 agonist or vehicle (dose volume 0.025 ml/kg) on the morning of day 1, and food intake is measured for 4 days after dosing. On the last day of each study, 4 days after dosing, a blood sample for measurement of plasma exposure of the GLP-1 agonist is taken from the heart in anaesthetised animals. The animals are thereafter euthanised with an intra-cardial overdose of pentobarbitone. Plasma content of the GLP-1 agonist is analysed using ELISA or a similar antibody based assay.

Food intake is calculated as mean±SEM 24 h food intake on the 4 days. Statistical comparisons of the 24 hour food intake in the vehicle vs. GLP-1 agonist group on the 4 days are done using one-way or two-way-ANOVA repeated measures, followed by Bonferroni post-test.

Assay (V): Stability Against Degradation by Intestinal Enzymes

The purpose of this example is to test the stability against degradation by intestinal enzymes. GLP-1 (7-37) may be used in the assay as a comparative compound. The strongest proteolytic activities in the intestine are of pancreatic origin and include the serine endopeptidases trypsin, chymotrypsin, and elastase as well as several types of carboxypeptidases. An assay with small intestine extract from rats was developed and used as described in the following.

Extracts from Rat Small Intestine

Small intestines are prepared from rats and flushed with 8 ml of 150 mM NaCl, 20 mM Hepes pH 7.4. The solutions are centrifuged for 15 min at 4,600 rpm in a Heraeus Multifuge 3 S-R centrifuge with a 75006445 rotor. The supernatants are removed and filtered through a 0.22 µm Millipore Millex GV PVDF membrane. Filtrates of several animals are pooled to average out individual differences.

The protein content of the obtained extracts is determined by Bradford Assay (see e.g. Analytical Biochemistry (1976), vol. 72, p. 248-254, and Analytical Biochemistry (1996), vol. 236 p. 302-308).

Degradation Assay 2.5 nmol of the GLP-1 agonists to be tested are incubated with the intestinal extract in a volume of 250 µl at 37° C. over a period of one hour. Intestinal samples are assayed in presence of 20 mM Hepes at pH 7.4. The concentration of the intestinal extract is titrated in pilot experiments so that the half-life (t½) of GLP-1 (7-37) is in the range of 10-20 minutes. The small intestine extract is used at a concentration of 1.4 µg/ml. All components except for the intestinal extract are mixed and pre-warmed for ten minutes at 37° C. Immediately after addition of the intestinal extract a sample of 50 µl is taken and mixed with the same volume of 1% trifluoroacetic acid (TFA). Further samples are taken accordingly after 15, 30, and 60 minutes.

Sample Analysis

UPLC Analysis:

10 µl of the samples are analysed by UPLC using a Waters Acquity system with a BEH C18 1.7 µm 2.1×50 mm column and a 30 to 65% gradient of 0.1% TFA and 0.07% TFA in acetonitrile over 5 minutes at a flow rate of 0.6 ml/min. After baseline subtraction the peak integrals of the intact compounds in the HPLC chromatogram recorded at a wavelength of 214 nm are determined.

MALDI-TOF Analysis:

1 µl of each sample is transferred to a Bruker/Eppendorf PAC HCCA 384 MALDI target. Analysis is performed with a Bruker Autoflex matrix-assisted laser desorption and ionisation-time of flight (MALDI-TOF) mass spectrometer using the pre-defined method "PAC_measure" with an extended detection range of 500 to 5000 Da and the pre-defined calibration method "PAC_calibrate".

Data Analysis:

The peak integrals of the HPLC chromatograms are plotted against time. The half-life of the respective compound is calculated by fitting the data using SigmaPlot 9.0 software and an equation for a 2-parameter exponential decay. For each GLP-1 agonist tested, the relative half-life (relative $T_{1/2}$) is calculated as the half-life ($T_{1/2}$) of the compound in question, divided by the half-life ($T_{1/2}$) of GLP-1 (7-37), determined in the same way.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A method for reducing body weight, comprising administering semaglutide once weekly in an amount of at least 0.7 mg and up to 1.6 mg to a subject in need thereof, wherein said semaglutide is administered without another therapeutic agent.

2. The method according to claim 1, wherein said semaglutide is administered in an amount of at least 0.8 mg per week.

3. The method according to claim 1, wherein said semaglutide is administered by parenteral administration.

4. The method according to claim 1, wherein said semaglutide is administered once weekly at about 0.8 mg.

5. The method according to claim 1, wherein the subject is suffering from type 2 diabetes.

6. The method according to claim 5, wherein said semaglutide is administered by subcutaneous injection.

* * * * *

SEQUENCE LISTING

```
<160> NUMBER OF SEQ ID NOS: 6

<210> SEQ ID NO 1
<211> LENGTH: 31
<212> TYPE: PRT
<213> ORGANISM: Homo sapiens

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 2
<211> LENGTH: 39
<212> TYPE: PRT
<213> ORGANISM: Artificial Sequence
<220> FEATURE:
<223> OTHER INFORMATION: GLP-1 agonist
<220> FEATURE:
<221> NAME/KEY: MISC_FEATURE
<222> LOCATION: (1)..(1)
<223> OTHER INFORMATION: This residue is H-His
<220> FEATURE:
<221> NAME/KEY: MISC_FEATURE
<222> LOCATION: (39)..(39)
<223> OTHER INFORMATION: This residue is Ser-NH2

<400> SEQUENCE: 2
```

```
His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35
```

<210> SEQ ID NO 3
<211> LENGTH: 30
<212> TYPE: PRT
<213> ORGANISM: Artificial Sequence
<220> FEATURE:
<223> OTHER INFORMATION: GLP-1 agonist
<220> FEATURE:
<221> NAME/KEY: MISC_FEATURE
<222> LOCATION: (2)..(2)
<223> OTHER INFORMATION: Aib
<220> FEATURE:
<221> NAME/KEY: MISC_FEATURE
<222> LOCATION: (29)..(29)
<223> OTHER INFORMATION: Aib

<400> SEQUENCE: 3

```
His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Lys Xaa Arg
            20                  25                  30
```

<210> SEQ ID NO 4
<211> LENGTH: 60
<212> TYPE: PRT
<213> ORGANISM: Artificial Sequence
<220> FEATURE:
<223> OTHER INFORMATION: GLP-1 agonist
<220> FEATURE:
<221> NAME/KEY: MISC_FEATURE
<222> LOCATION: (60)..(60)
<223> OTHER INFORMATION: genetically fused to human albumin

<400> SEQUENCE: 4

```
His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg His Gly
            20                  25                  30

Glu Gly Thr Phe Thr Ser Asp Val Ser Ser Tyr Leu Glu Gly Gln Ala
        35                  40                  45

Ala Lys Glu Phe Ile Ala Trp Leu Val Lys Gly Arg
    50                  55                  60
```

<210> SEQ ID NO 5
<211> LENGTH: 40
<212> TYPE: PRT
<213> ORGANISM: Artificial Sequence
<220> FEATURE:
<223> OTHER INFORMATION: GLP-1 agonist
<220> FEATURE:
<221> NAME/KEY: MISC_FEATURE
<222> LOCATION: (1)..(1)
<223> OTHER INFORMATION: L-histidine, D-histidine, desamino-histidine,
    2-amino-histidine, beta-hydroxy-histidine, homohistidine, Nalpha-
    acetyl-histidine, alpha-fluoromethyl-histidine, alpha-methyl-
    histidine, 3-pyridylalanine, 2-pyridylalanine or 4-pyridylalanine
<220> FEATURE:
<221> NAME/KEY: MISC_FEATURE
<222> LOCATION: (2)..(2)
<223> OTHER INFORMATION: Ala, Gly, Val, Leu, Ile, Lys, Aib,
    (1-aminocyclopropyl)carboxylic acid, (1-aminocyclobutyl)carboxylic

```
      acid, (1-aminocyclopentyl)carboxylic acid,
      (1-aminocyclohexyl)carboxylic acid,
<220> FEATURE:
<221> NAME/KEY: MISC_FEATURE
<222> LOCATION: (10)..(10)
<223> OTHER INFORMATION: Val or Leu
<220> FEATURE:
<221> NAME/KEY: MISC_FEATURE
<222> LOCATION: (12)..(12)
<223> OTHER INFORMATION: Ser, Lys or Arg
<220> FEATURE:
<221> NAME/KEY: MISC_FEATURE
<222> LOCATION: (13)..(13)
<223> OTHER INFORMATION: Tyr or Gln
<220> FEATURE:
<221> NAME/KEY: MISC_FEATURE
<222> LOCATION: (14)..(14)
<223> OTHER INFORMATION: Leu or Met
<220> FEATURE:
<221> NAME/KEY: MISC_FEATURE
<222> LOCATION: (16)..(16)
<223> OTHER INFORMATION: Gly, Glu or Aib
<220> FEATURE:
<221> NAME/KEY: MISC_FEATURE
<222> LOCATION: (17)..(17)
<223> OTHER INFORMATION: Gln, Glu, Lys or Arg
<220> FEATURE:
<221> NAME/KEY: MISC_FEATURE
<222> LOCATION: (19)..(19)
<223> OTHER INFORMATION: Ala or Val
<220> FEATURE:
<221> NAME/KEY: MISC_FEATURE
<222> LOCATION: (20)..(20)
<223> OTHER INFORMATION: Lys, Glu or Arg
<220> FEATURE:
<221> NAME/KEY: MISC_FEATURE
<222> LOCATION: (21)..(21)
<223> OTHER INFORMATION: Glu or Leu
<220> FEATURE:
<221> NAME/KEY: MISC_FEATURE
<222> LOCATION: (24)..(24)
<223> OTHER INFORMATION: Ala, Glu or Arg
<220> FEATURE:
<221> NAME/KEY: MISC_FEATURE
<222> LOCATION: (27)..(27)
<223> OTHER INFORMATION: Val or Lys
<220> FEATURE:
<221> NAME/KEY: MISC_FEATURE
<222> LOCATION: (28)..(28)
<223> OTHER INFORMATION: Lys, Glu, Asn or Arg
<220> FEATURE:
<221> NAME/KEY: MISC_FEATURE
<222> LOCATION: (29)..(29)
<223> OTHER INFORMATION: Gly or Aib
<220> FEATURE:
<221> NAME/KEY: MISC_FEATURE
<222> LOCATION: (30)..(30)
<223> OTHER INFORMATION: Arg, Gly or Lys
<220> FEATURE:
<221> NAME/KEY: MISC_FEATURE
<222> LOCATION: (31)..(31)
<223> OTHER INFORMATION: Gly, Ala, Glu, Pro, Lys, amide or absent
<220> FEATURE:
<221> NAME/KEY: MISC_FEATURE
<222> LOCATION: (32)..(32)
<223> OTHER INFORMATION: Lys, Ser, amide or absent
<220> FEATURE:
<221> NAME/KEY: MISC_FEATURE
<222> LOCATION: (33)..(33)
<223> OTHER INFORMATION: Ser, Lys, amide or absent, provided that this
      residue is absent if any of the preceding residues are absent
<220> FEATURE:
<221> NAME/KEY: MISC_FEATURE
<222> LOCATION: (34)..(34)
<223> OTHER INFORMATION: Gly, amide or absent, provided that this
      residue is absent if any of the preceding residues are absent
<220> FEATURE:
<221> NAME/KEY: MISC_FEATURE
<222> LOCATION: (35)..(35)
```

```
<223> OTHER INFORMATION: Ala, amide or absent, provided that this
      residue is absent if any of the preceding residues are absent
<220> FEATURE:
<221> NAME/KEY: MISC_FEATURE
<222> LOCATION: (36)..(36)
<223> OTHER INFORMATION: Pro, amide or absent, provided that this
      residue is absent if any of the preceding residues are absent
<220> FEATURE:
<221> NAME/KEY: MISC_FEATURE
<222> LOCATION: (37)..(37)
<223> OTHER INFORMATION: Pro, amide or absent, provided that this
      residue is absent if any of the preceding residues are absent
<220> FEATURE:
<221> NAME/KEY: MISC_FEATURE
<222> LOCATION: (38)..(38)
<223> OTHER INFORMATION: Pro, amide or absent, provided that this
      residue is absent if any of the preceding residues are absent
<220> FEATURE:
<221> NAME/KEY: MISC_FEATURE
<222> LOCATION: (39)..(39)
<223> OTHER INFORMATION: Ser, amide or absent, provided that this
      residue is absent if any of the preceding residues are absent
<220> FEATURE:
<221> NAME/KEY: MISC_FEATURE
<222> LOCATION: (40)..(40)
<223> OTHER INFORMATION: amide or absent, provided that this residue is
      absent if any of the preceding residues are absent

<400> SEQUENCE: 5

Xaa Xaa Glu Gly Thr Phe Thr Ser Asp Xaa Ser Xaa Xaa Xaa Glu Xaa
1               5                   10                  15

Xaa Ala Xaa Xaa Xaa Phe Ile Xaa Trp Leu Xaa Xaa Xaa Xaa Xaa Xaa
            20                  25                  30

Xaa Xaa Xaa Xaa Xaa Xaa Xaa Xaa
        35                  40

<210> SEQ ID NO 6
<211> LENGTH: 32
<212> TYPE: PRT
<213> ORGANISM: Artificial Sequence
<220> FEATURE:
<223> OTHER INFORMATION: GLP-1 agonist
<220> FEATURE:
<221> NAME/KEY: MISC_FEATURE
<222> LOCATION: (1)..(1)
<223> OTHER INFORMATION: L-histidine, D-histidine, desamino-histidine,
      2-amino-histidine, -hydroxy-histidine, homohistidine, Nalpha-
      acetyl-histidine, alpha-fluoromethyl-histidine, alpha-methyl-
      histidine, 3-pyridylalanine, 2-pyridylalanine or 4-pyridylalanine
<220> FEATURE:
<221> NAME/KEY: MISC_FEATURE
<222> LOCATION: (2)..(2)
<223> OTHER INFORMATION: Ala, Gly, Val, Leu, lle, Lys, Aib,
      (1-aminocyclopropyl)carboxylic acid, (1-aminocyclobutyl)carboxylic
      acid, (1-aminocyclopentyl)carboxylic acid,
      (1-aminocyclohexyl)carboxylic acid, (1-aminocycloheptyl)carboxylic
      acid, or
<220> FEATURE:
<221> NAME/KEY: MISC_FEATURE
<222> LOCATION: (12)..(12)
<223> OTHER INFORMATION: Ser, Lys or Arg
<220> FEATURE:
<221> NAME/KEY: MISC_FEATURE
<222> LOCATION: (16)..(16)
<223> OTHER INFORMATION: Gly, Glu or Aib
<220> FEATURE:
<221> NAME/KEY: MISC_FEATURE
<222> LOCATION: (17)..(17)
<223> OTHER INFORMATION: Gln, Glu, Lys or Arg
<220> FEATURE:
<221> NAME/KEY: MISC_FEATURE
<222> LOCATION: (20)..(20)
<223> OTHER INFORMATION: Lys, Glu or Arg
<220> FEATURE:
<221> NAME/KEY: MISC_FEATURE
```

```
<222> LOCATION: (24)..(24)
<223> OTHER INFORMATION: Ala, Glu or Arg
<220> FEATURE:
<221> NAME/KEY: MISC_FEATURE
<222> LOCATION: (28)..(28)
<223> OTHER INFORMATION: Lys, Glu or Arg
<220> FEATURE:
<221> NAME/KEY: MISC_FEATURE
<222> LOCATION: (29)..(29)
<223> OTHER INFORMATION: Gly or Aib
<220> FEATURE:
<221> NAME/KEY: MISC_FEATURE
<222> LOCATION: (30)..(30)
<223> OTHER INFORMATION: Arg or Lys
<220> FEATURE:
<221> NAME/KEY: MISC_FEATURE
<222> LOCATION: (31)..(31)
<223> OTHER INFORMATION: Gly, Ala, Glu or Lys
<220> FEATURE:
<221> NAME/KEY: MISC_FEATURE
<222> LOCATION: (32)..(32)
<223> OTHER INFORMATION: Lys, amide or is absent

<400> SEQUENCE: 6

Xaa Xaa Glu Gly Thr Phe Thr Ser Asp Val Ser Xaa Tyr Leu Glu Xaa
1               5                   10                  15

Xaa Ala Ala Xaa Glu Phe Ile Xaa Trp Leu Val Xaa Xaa Xaa Xaa Xaa
            20                  25                  30
```